United States Patent [19]
Lee

[11] Patent Number: 5,594,235
[45] Date of Patent: Jan. 14, 1997

[54] AUTOMATED SURFACE ACQUISITION FOR A CONFOCAL MICROSCOPE

[75] Inventor: Ken K. Lee, Los Altos, Calif.

[73] Assignee: Ultrapointe Corporation, San Jose, Calif.

[21] Appl. No.: 483,234

[22] Filed: Jun. 7, 1995

Related U.S. Application Data

[63] Continuation-in-part of Ser. No. 80,014, Jun. 17, 1993, Pat. No. 5,479,252, and a continuation-in-part of Ser. No. 183,536, Jan. 18, 1994, Pat. No. 5,483,055.

[51] Int. Cl.$^6$ .................................................. G01J 1/20
[52] U.S. Cl. ..................... 250/201.3; 250/216; 359/368; 359/813
[58] Field of Search ........................... 250/201.2, 201.3, 250/204, 216; 359/368, 371, 381, 813, 823

[56] References Cited

U.S. PATENT DOCUMENTS

| | | | |
|---|---|---|---|
| 4,863,252 | 9/1989 | McCarthy et al. | 359/813 |
| 5,084,612 | 1/1992 | Iwashi et al. | 250/201.3 |
| 5,479,252 | 12/1995 | Worster et al. | 250/559.42 |
| 5,483,055 | 1/1996 | Thompson et al. | 359/368 |

*Primary Examiner*—Stephone Allen
*Attorney, Agent, or Firm*—Skjerven, Morrill, MacPherson, Franklin & Friel

[57] ABSTRACT

A method is described for obtaining an image of a target surface with a confocal microscope. The surface to be imaged is represented by a number of points on the surface, each of which has a unique location represented by X, Y, and Z Cartesian coordinates. The microscope selects a starting position for an objective lens of the microscope along a Z vector substantially normal to the surface. The objective lens has a preselected range of travel along the Z vector that is divided into a number of Z positions. Next, the objective lens is positioned and the surface scanned at each of the Z positions. The scan at each Z position provides signals, one for each point on the surface, representing the reflected intensity of laser light. Then, for each point on the surface, the microscope finds the Z coordinate of the point by determining which Z position resulted in the greatest return intensity of reflected laser light. From this information the Z coordinate of any particular point may be determined because the maximum reflected intensity for a given point, when correlated to the Z position of the objective lens, gives the Z location of that point on the surface. Having determined the Z locations for each point on the surface, the Z locations are compared to determine the low and high points on the surface. A second scan is then set up using the low and high points on the surface to determine the optimal scan parameters.

10 Claims, 17 Drawing Sheets

KEY TO FIG. 5d

| FIG. 5d-1 | FIG. 5d-2 | FIG. 5d-3 |

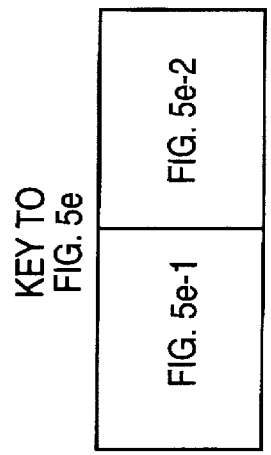
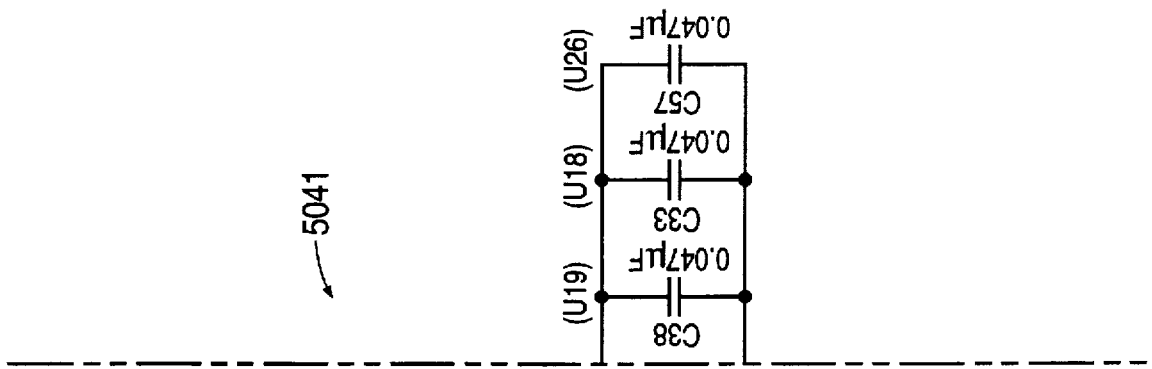

AUTOMATED SURFACE ACQUISITION FOR A CONFOCAL MICROSCOPE

CROSS-REFERENCE TO RELATED APPLICATIONS

The present application is a continuation-in-part of commonly owned application Ser. No. 08/080,014, now U.S. Pat. No. 5,479,252, filed Jun. 17, 1993, entitled "Laser Imaging System For Inspection and Analysis of Sub-Micron Particles," by Bruce W. Worster, Dale E. Crane, Hans J. Hansen, Christopher R. Fairley, and Ken K. Lee, and commonly owned application Ser. No. 08/183,536, now U.S. Pat. No. 5,483,055, filed Jan. 18, 1994, entitled "A Method and Apparatus for Performing an Automatic Focus Operation," by Timothy V. Thompson, Christopher R. Fairley, and Ken K. Lee; and is related to the commonly owned, co-pending U.S. patent applications entitled "Surface Extraction from a Three-Dimensional Data Set," by Ken K. Lee, application Ser. No. 08/079,193, filed on Jun. 17, 1993, and "Surface Data Processor," by Abigail A. Moorhouse, Christopher R. Fairley, Phillip R. Rigg, and Alan Helgesson. These applications are incorporated herein by this reference.

COPYRIGHTED MATERIAL

A portion of the disclosure of this patent document contains material that is subject to copyright protection. The copyright owner has no objection to the facsimile reproduction by anyone of the patent document or the patent disclosure, as it appears in the Patent and Trademark Office patent files and records, but otherwise reserves all copyrights.

BACKGROUND

Semiconductor chip manufacturers have increasingly sought to improve yields in their production processes. Key to this effort is the identification of particulate contamination and wafer defects during wafer processing. One tool available to identify contamination and defects is a laser imaging system that utilizes confocal laser scanning microscopy techniques, also known as a confocal microscope. Such a microscope includes a laser light source that emits a laser beam focussed on a pinhole aperture in a focal plane of an objective lens. A beam scanner receives the beam after it exits the pinhole aperture and, using moving reflective elements, scans the beam through the objective lens and across a surface to be imaged.

The objective lens has a second focal plane, on the side of the objective lens opposite the pinhole aperture, in which an image of the pinhole aperture is formed. A photodetector in the return path of laser light reflected from the surface generates an output signal proportional to the intensity of laser light reflected from the object and back through the lens, the beam scanner, and the pinhole aperture. For a given point on the surface, the reflected intensity, and therefore the output signal from the photodetector, is highest when the surface lies in the second focal plane of the lens. This is because the objective lens focusses the reflected image of the pinhole aperture back through the pinhole aperture to the photodetector. In contrast, when the surface does not lie in the second focal plane, the image of the pinhole aperture is out of focus (i.e., the diameter of the image on the surface is much larger than the aperture) so that most of the reflected image does not return through the pinhole aperture.

To obtain an image of a target surface, the target surface is scanned in a number of X-Y planes located along a Z axis generally normal to the target surface. In each scan, the photodetector provides indications of the intensities of the reflected laser light from a number of points on the surface. That is, the objective lens is positioned at each location on the Z axis and the laser beam is scanned across the surface to generate a number of signals, each of the signals representing an intensity of light reflected through the objective lens from a given point on the surface. The group of signals provided by an X-Y scan from a single location of the objective lens on the Z axis is called a "slice" of intensity data. Slices taken from the various locations on the Z axis overlap to form a three-dimensional set of reflected intensity data.

The overlapping slices of data create a column of data values for each point on the surface, each data value representing a reflected intensity of light from that point from a particular Z location. For each such column, data values are compared to determine the location on the Z axis that resulted in a maximum reflected intensity. Because the intensity of the reflected light from a particular point is greatest when that point on the surface is coincident with the focal plane of the objective lens, the location of the objective lens on the Z axis that corresponds to the maximum reflected intensity gives an indication of the Z coordinate of that point on the surface. In this way, the X, Y, and Z Cartesian coordinates are determined for each point on the surface. An image of the surface may then be generated from this information.

For a more detailed description of such a laser imaging system, see the co-pending application entitled "Laser Imaging System For Inspection and Analysis of Sub-Micron Particles," the content of which is incorporated herein by reference.

Confocal microscopes require the user to input sample-specific data before an image of the target sample can be obtained. For example, the user might have to specify the optimal photodetector gain for measuring laser-light reflected from the target surface, the offset in the Z-direction from which the first X-Y scan will begin, the range to be covered in the Z direction, and the optimal number of "slices" taken along the Z axis to form the three-dimensional set of reflected intensity data.

Assume, for example, that time constraints limit the number of slices to fifty. If the sample is very flat, resolution should be maximized by taking the fifty slices over a relatively short Z range, whereas if the surface of the sample is relatively rough (i.e., the surface features are "tall"), the distance between adjacent slices should be optimized so that the total Z range captures the low and high regions of the surface. And, whatever the surface texture, the scan range should be optimized so that the scan precisely covers the Z range of the surface features so that almost all of the fifty slices provide surface data.

Unfortunately, the process of setting up a confocal microscope for different types of target samples can be difficult and tedious. There is therefore a need to obtain a surface image using a confocal microscope without requiring the user to manually optimize scan parameters.

SUMMARY

The present invention fills the need for a confocal microscope that automatically sets the optimal vertical scan range (i.e., Z-scan range) and photodetector gain for a given target sample. In accordance with this invention, a user is able to automatically set the Z-scan start point, Z-scan range, and optimal photodetector gain. A manual method of setting the scan parameters is still supported, and may be needed in special circumstances, as where the surface features are very tall, or for multi-layered samples.

In one embodiment, a button, called the "SetZ" button, is provided to allow the user to enter the automatic mode. When a user presses the SetZ button, the program performs a number of scans along the Z axis over a scan range that is long relative to typical surface features. From this, the system obtains a coarse measurement of highest and lowest points on the surface (i.e., the greatest and the least Z values on the scanned surface). The system then uses this information to set the Z positions at which the Z stage will start and stop during a subsequent series of scans.

The Z-scan starting point for the microscope on the Z axis is set to the Z position corresponding to the highest point on the surface plus a safety margin. Similarly, the end Z position is set to the lowest point measured minus a safety margin. The laser imaging system also uses the maximum reflected intensity obtained from the SetZ scan to set the optimal photodetector gain, and therefore the perceived reflected laser intensity, for the sample.

Having determined and set the photodetector gain, Z-scan start position, and the Z-scan stop position, the system evenly divides the distance between the start and stop positions by one less than the number of available Z-steps and moves the fine Z stage to the start Z position.

The system may then image the target surface by (1) taking a selected number of slices of intensity data along the Z axis (e.g., fifty slices) from the Z-scan start position to the Z-scan stop position and (2) using the data obtained to determine the location of a number of points on the surface of the target surface.

DETAILED DESCRIPTION

Figure 1:
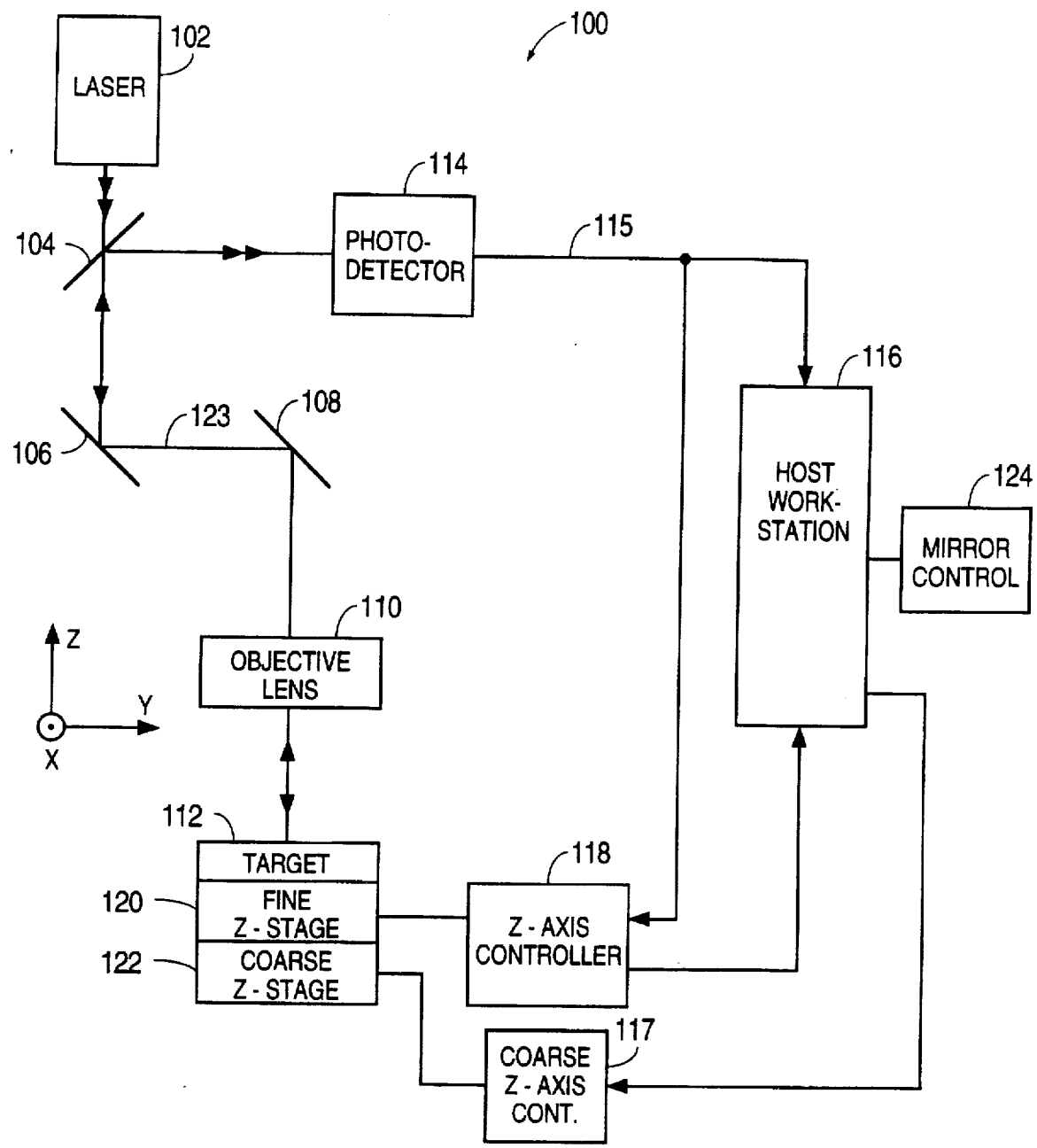
FIG. 1 is a simplified block diagram of a confocal microscope system according to an embodiment of the invention.

FIG. 1 is a simplified block diagram of a confocal microscope system 100 according to an embodiment of the invention. A confocal microscope system with which the method according to the invention can be used is described in more detail in commonly owned U.S. patent application, Ser. No. 08/080,014, entitled "Laser Imaging System for Inspection and Analysis of Sub-Micron Particles," the disclosure of which is incorporated herein by reference. A laser 102 generates a laser beam 123 that is transmitted through a beam splitter 104, reflected from an X-mirror 106 and a Y-mirror 108, and transmitted through an objective lens 110 to the surface of a target 112. In one embodiment, laser 102 is a conventional argon-ion laser, however, other types of lasers may be utilized in alternate embodiments.

Target 112 is an object, such as a semiconductor wafer, that is to be viewed using microscope system 100. X-mirror 106 and Y-mirror 108 are each rotatable about an axis such that laser beam 123 can be moved along an X-axis and a Y-axis, respectively, of target 112. Laser 102, beam splitter 104, X-mirror 106, Y-mirror 108 and objective lens 110 are each conventional structures that are well known by those skilled in the art.

Figure 2A:
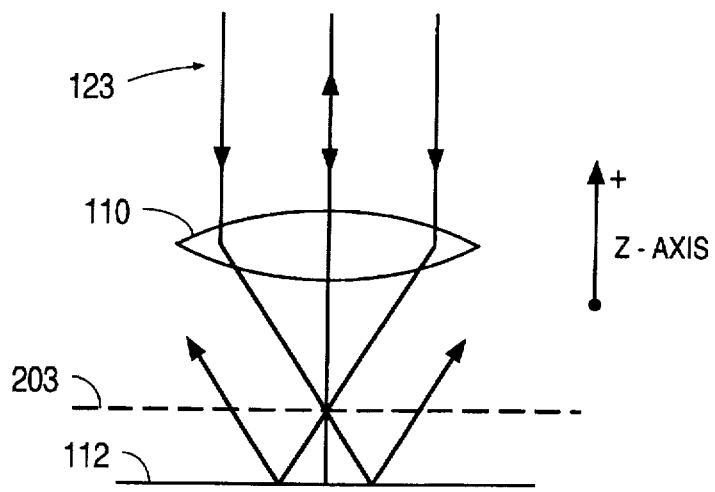
FIGS. 2a–2c show a target of a confocal microscope below the focus position, at the focus position and above the focus position, respectively, illustrating, at each position, the pattern of light reflected from the target.
Figure 2B:
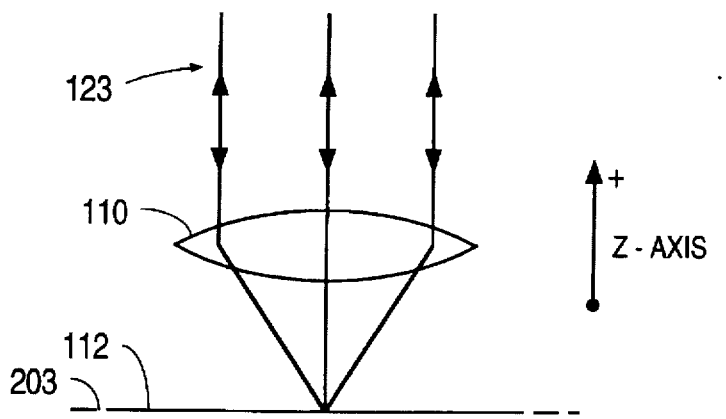
Figure 2C:
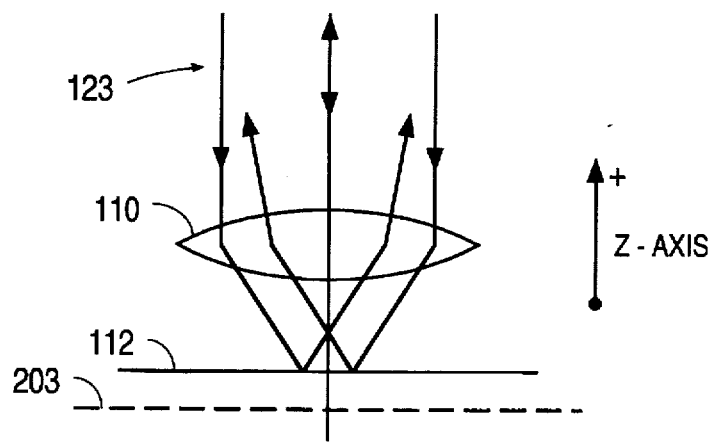

Laser beam 123 reflects off the surface of target 112 in a manner that is dependent upon the distance of objective lens 110 from target 112. FIGS. 2a–2c show target 112 below the focus position 203, at the focus position 203 and above the focus position 203, respectively, illustrating, at each position, the pattern of light reflected from target 112.

As illustrated in FIGS. 2a and 2c, when target 112 is positioned below or above the focus position 203, respectively, a small percentage of the laser light originally transmitted through objective lens 110 will be reflected back through objective lens 110 in a coherent manner. However, as shown in FIG. 2b, when target 112 is positioned at the focus position 203, substantially all of the reflected laser beam 123 is transmitted back through objective lens 110.

Referring again to FIG. 1, laser beam 123 is reflected from target 112 back through objective lens 110 to Y-mirror 108, X-mirror 106, and beam splitter 104. A mirror control 124 is coupled between a host work station 116 and X and Y mirror 106 and 108. Mirror control 124 is used by the work station to rotate X-mirror 106 and Y-mirror 108 such that laser beam 123 can scan more than a single point on target 112.

Beam splitter 104 routes the reflected beam to a photodetector 114. Photodetector 114 is a device such as a photo-multiplier tube (PMT) or photo-diode that generates an analog electronic focus signal on lead 115 proportional to the intensity of reflected laser beam 123 measured by photodetector 114. The photodetector gain must be appropriately calibrated for the laser power, laser wavelength and type of target 112 being viewed. This calibration is discussed below in connection with FIGS. 6A and 6B. In one embodiment, the PMT used is a Hamamatsu PMT, part number R268.

The electric focus signal on lead 115 is provided to host work station 116 and to Z-axis controller 118. Z-axis controller 118 is directly coupled to fine Z-stage 120 and is indirectly coupled to coarse Z-stage 122 through host work station 116 and coarse Z-axis controller 117. Coarse Z-stage 122 uses a motor, such as a stepper motor, to move target 112 through a relatively large range of motion along the Z-axis. In one embodiment of the present invention, the coarse Z-stage controller 117 is a conventional stepper motor controller available as part number 310MX3 from New England Affiliated Technology, and coarse Z-stage 122 is driven by a conventional stepper motor such as the Vexta C5858-9012 available from Oriental Motor. As explained in more detail below, fine Z-stage 120 uses a piezoelectrically driven element to move target 112 through a smaller range of motion along the Z-axis than coarse Z-stage 122. Although the invention is described as having a movable target 112 and a stationary objective lens 110, it is understood that target 112 can be held stationary while objective lens 110 is moved or both can be moved relative to each other.

Figure 3:
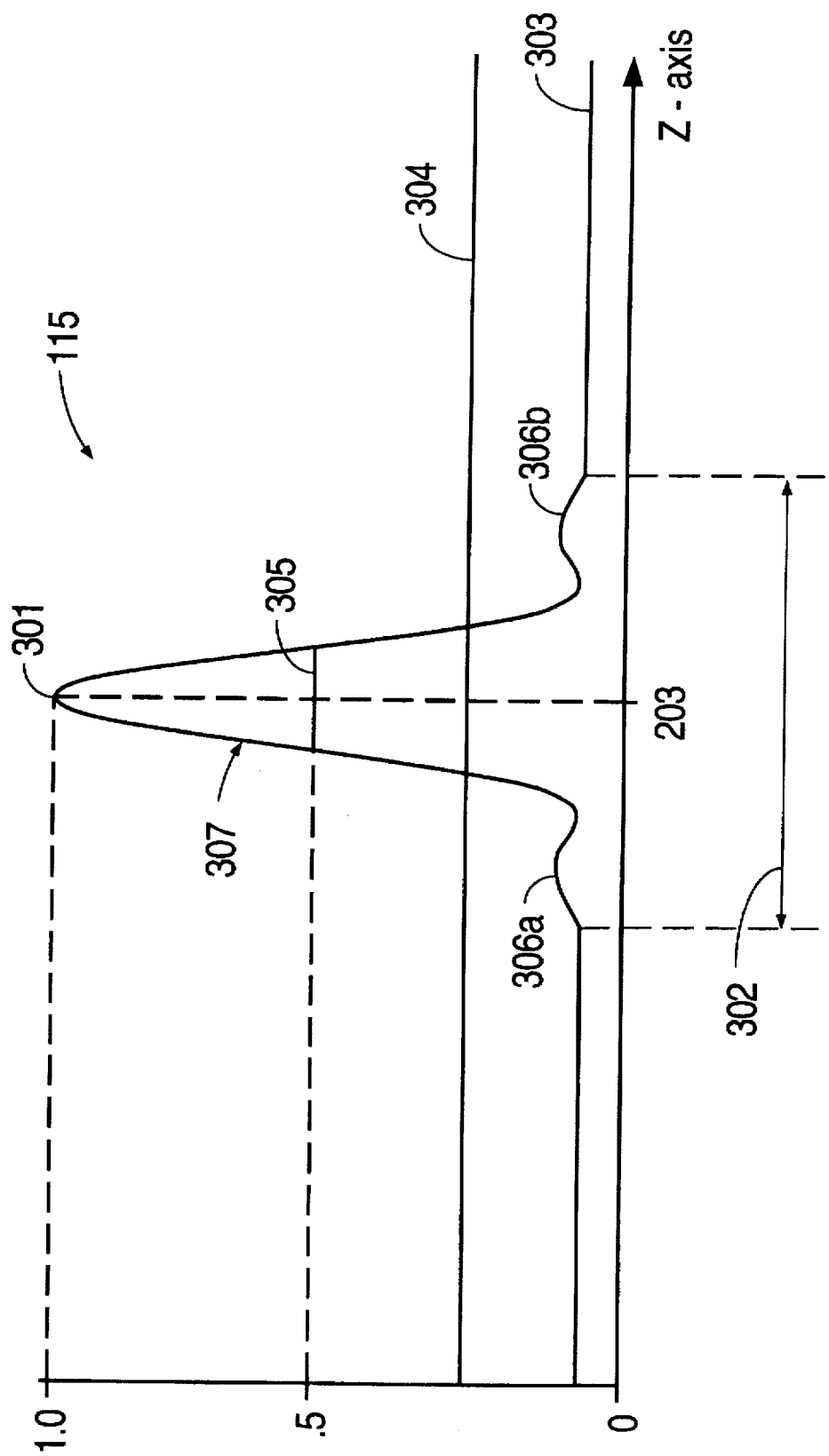
FIG. 3 is an idealized graph of an electronic focus signal of a confocal scanning laser microscope as the target is moved along the Z-axis.

FIG. 3 is an idealized graph of the electric focus signal on lead 115 as target 112 is moved along the Z-axis relative to objective lens 110. The electric focus signal on lead 115 is theoretically a sinc-squared function $((\sin(x)/x)^2)$ having a full-width, half-max measurement 305 that varies based on the numerical aperture of the objective lens 110 and the wavelength of laser beam 123. The full-width, half-max measurement 305 is the width of the electric focus signal on lead 115 (along the Z-axis) at the point on the Z axis at which the electric focus signal on lead 115 is at half of its maximum amplitude. For example, an objective lens 110 having a power of 100× and a numerical aperture of 0.95 and a laser beam 123 with a wavelength of 488 nanometers (nm) will produce an electronic focus signal on lead 115 with a full-width, half-max measurement of approximately 0.5 microns.

The electric focus signal on lead 115 exhibits a distinct focus position 203 in main lobe 307 as shown by peak 301. The electric focus signal also exhibits two side lobes 306a–306b. The depth of focus 302 is defined by the Z-axis range at which the magnitude of the electric focus signal on lead 115 is greater than a background value 303. The small non-zero background value 303 of the electronic focus signal on lead 115 results from leakage currents and the small amount of background light that reaches photodetector 114. The depth of focus 302 becomes smaller as the numerical aperture of objective lens 110 increases or as the wavelength of the laser beam 123 decreases. In the following discussion, the objective lens 110 has a power of 100× and numerical aperture of 0.95, and laser beam 123 has a wavelength of 488 nm, unless otherwise noted.

Figure 4:
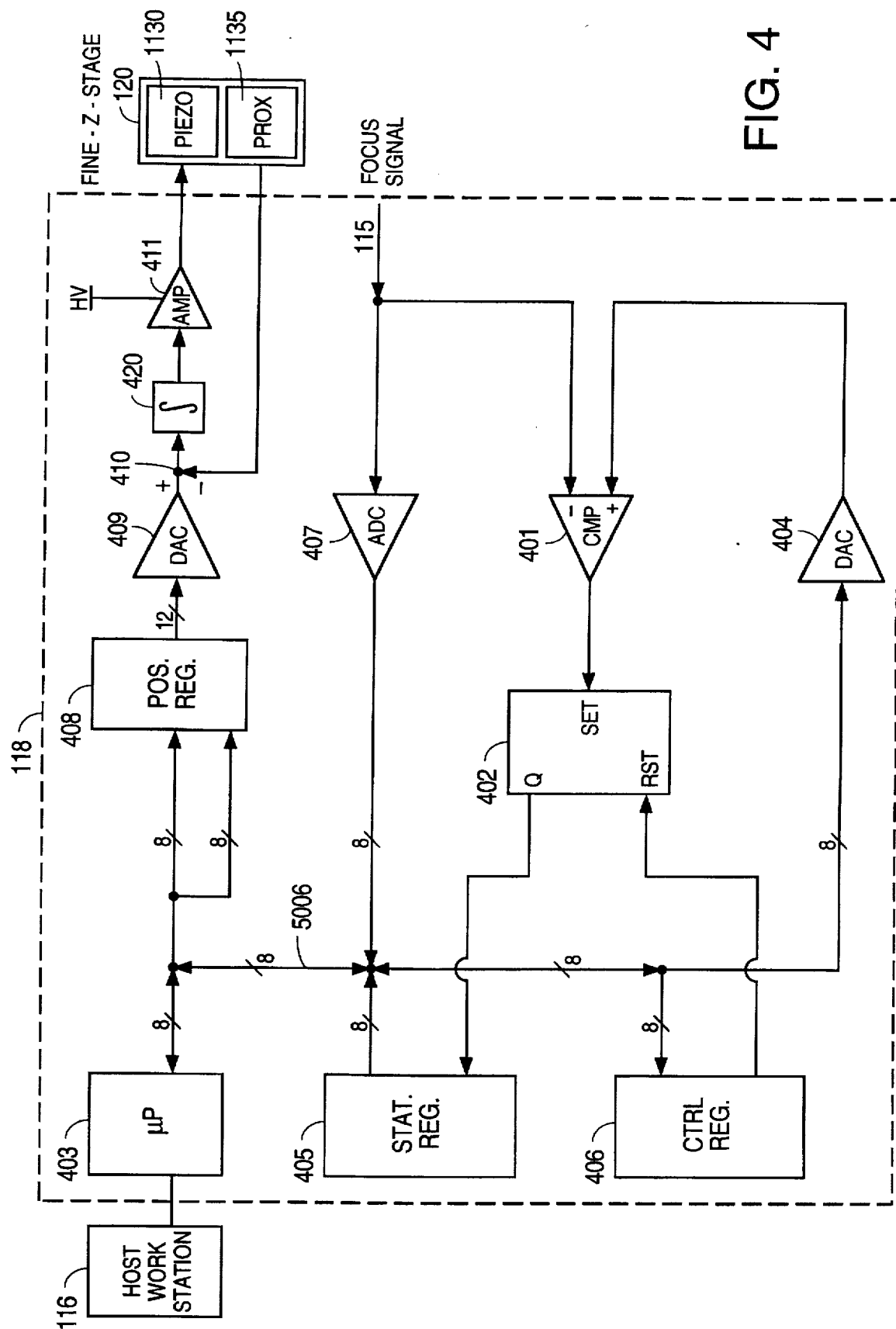
FIG. 4 is a block diagram of a Z-axis controller used to control a fine Z-stage and to provide feedback to a coarse Z-stage.

FIG. 4 is a block diagram of Z-axis controller 118, which controls the fine Z-stage 120 and also provides feedback used to control coarse Z-stage 122. Within Z-axis controller 118, the electric focus signal on lead 115 is transmitted to a first input terminal of comparator 401 and to an input of an analog to digital converter (ADC) 407. The output of ADC 407 is coupled to a microprocessor 403, which monitors and controls various components of the microscope, as described below.

The output terminal of comparator 401 is coupled to the set terminal of latching flip-flop 402. The Q output terminal of flip-flop 402 is coupled to an input of status register 405. An output signal from control register 406 is coupled to the reset terminal of flip-flop 402. The microprocessor 403 is coupled to status register 405, control register 406, digital to analog converter (DAC) 404, ADC 407 and host work station 116. The output terminal of DAC 404 is coupled to a second input terminal of comparator 401. Microprocessor 403 is also coupled to position control register 408. The output signal from position control register 408 is transmitted through DAC 409, integrator 420, summing node 410 and amplifier 411 to provide a control voltage to a piezoelectric element 1130 of the fine Z-stage 120. The summing node 410 also receives a feedback signal from a proximity sensor 1135 of the fine Z-stage 120.

Figures 1, 5A:
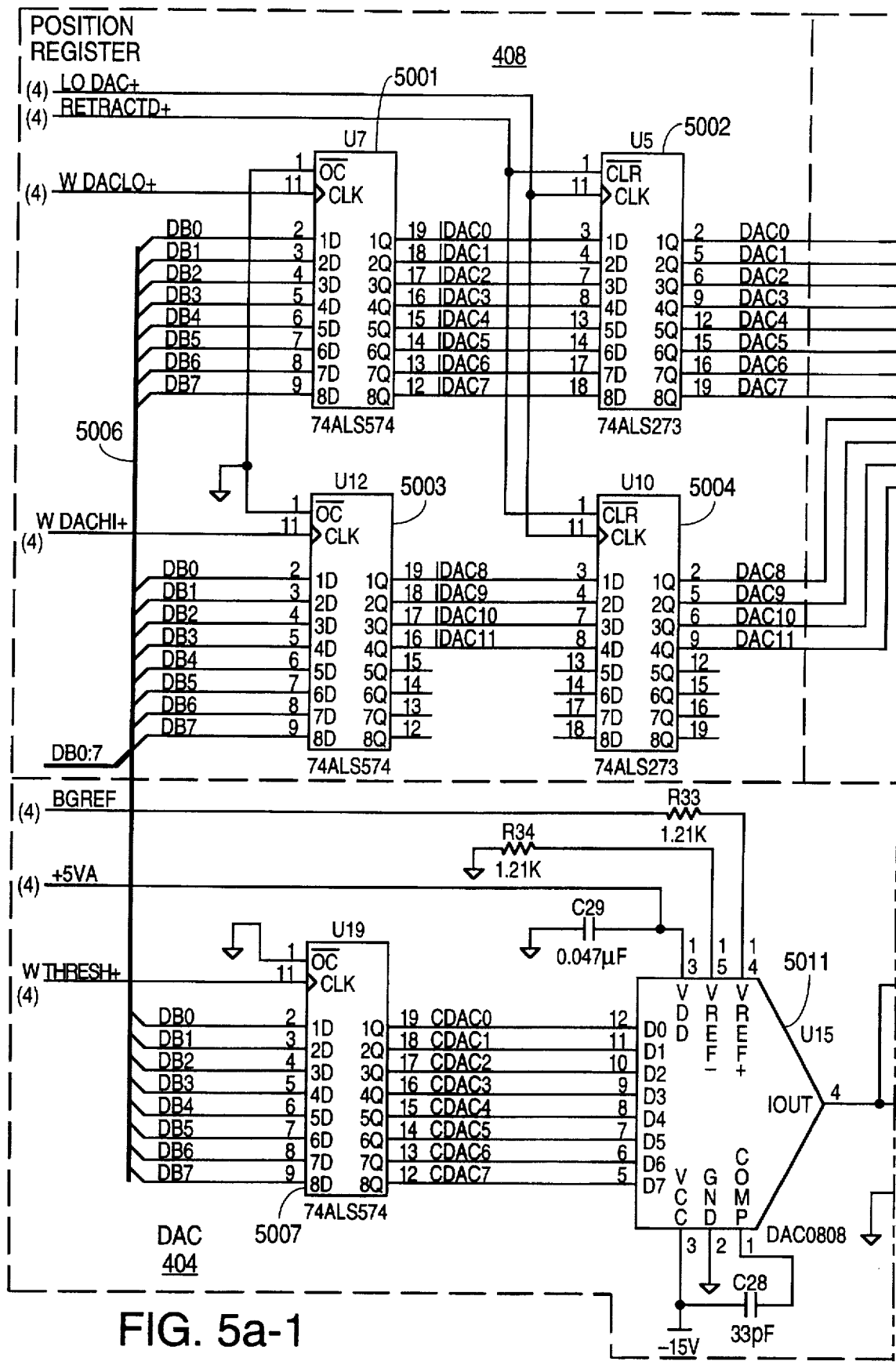
FIGS. 5a–5e are schematic diagrams of the Z-axis controller of FIG. 4.
Figures 2, 5A:
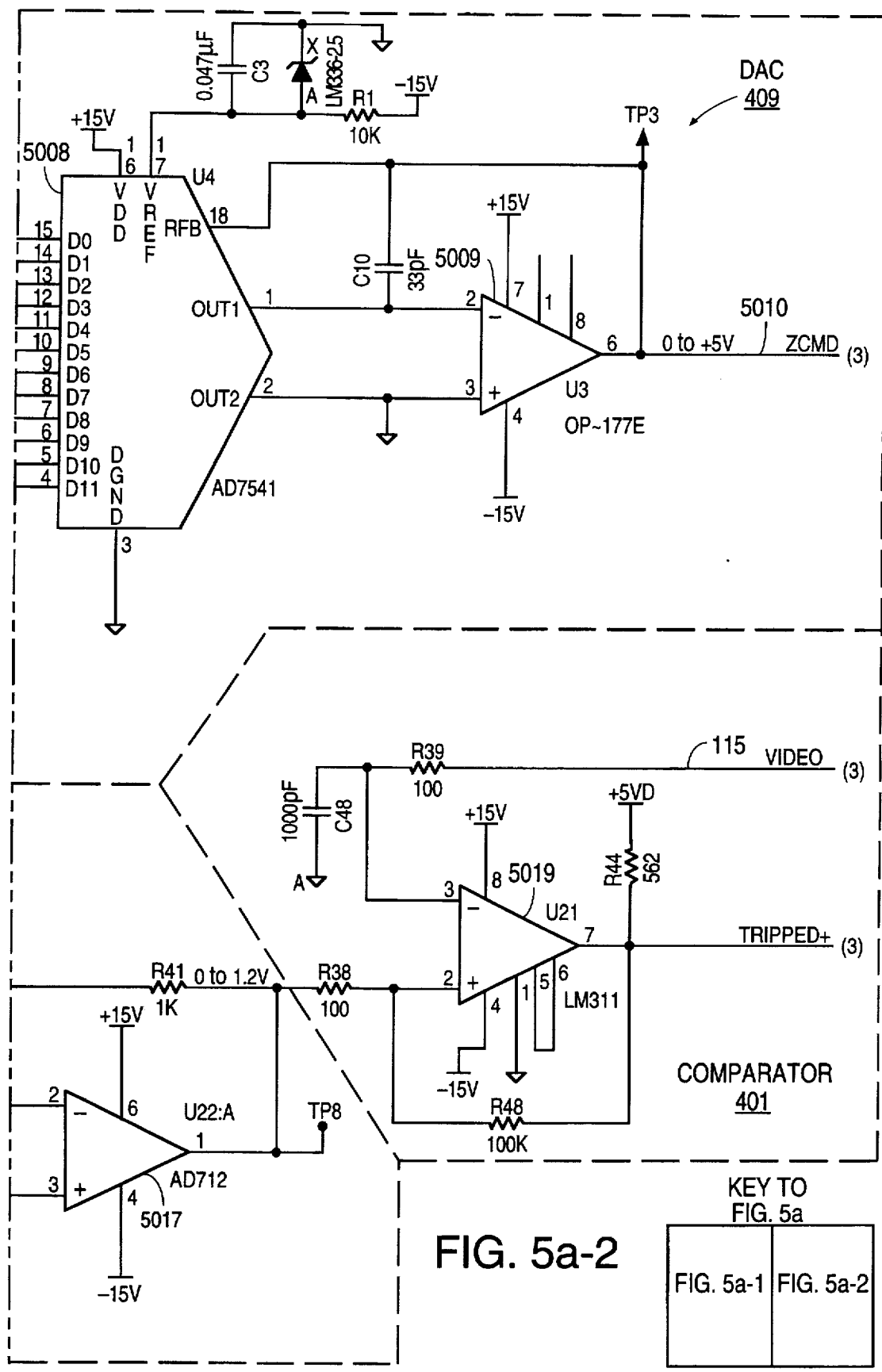
Figures 1, 5B:
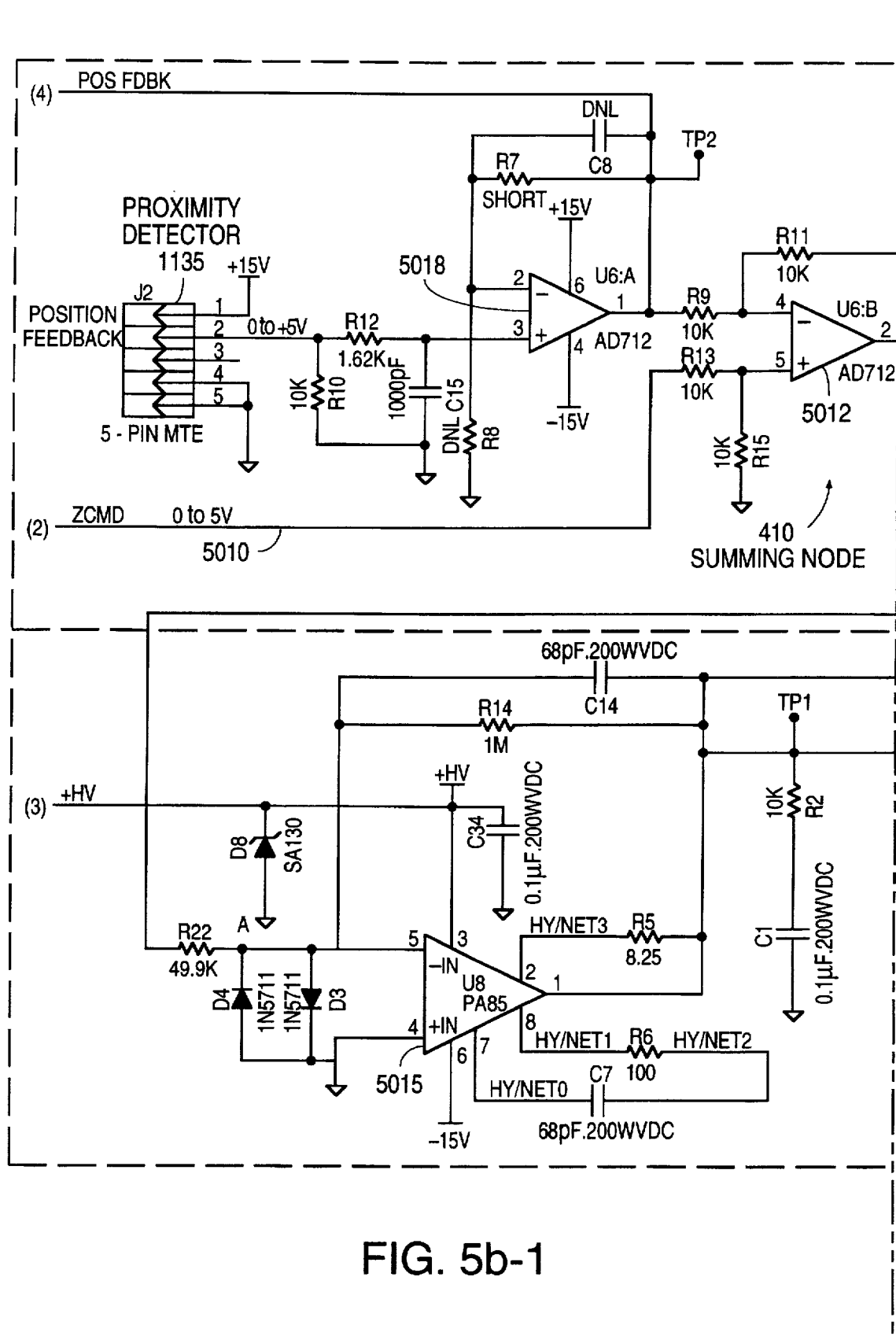
Figures 2, 5B:
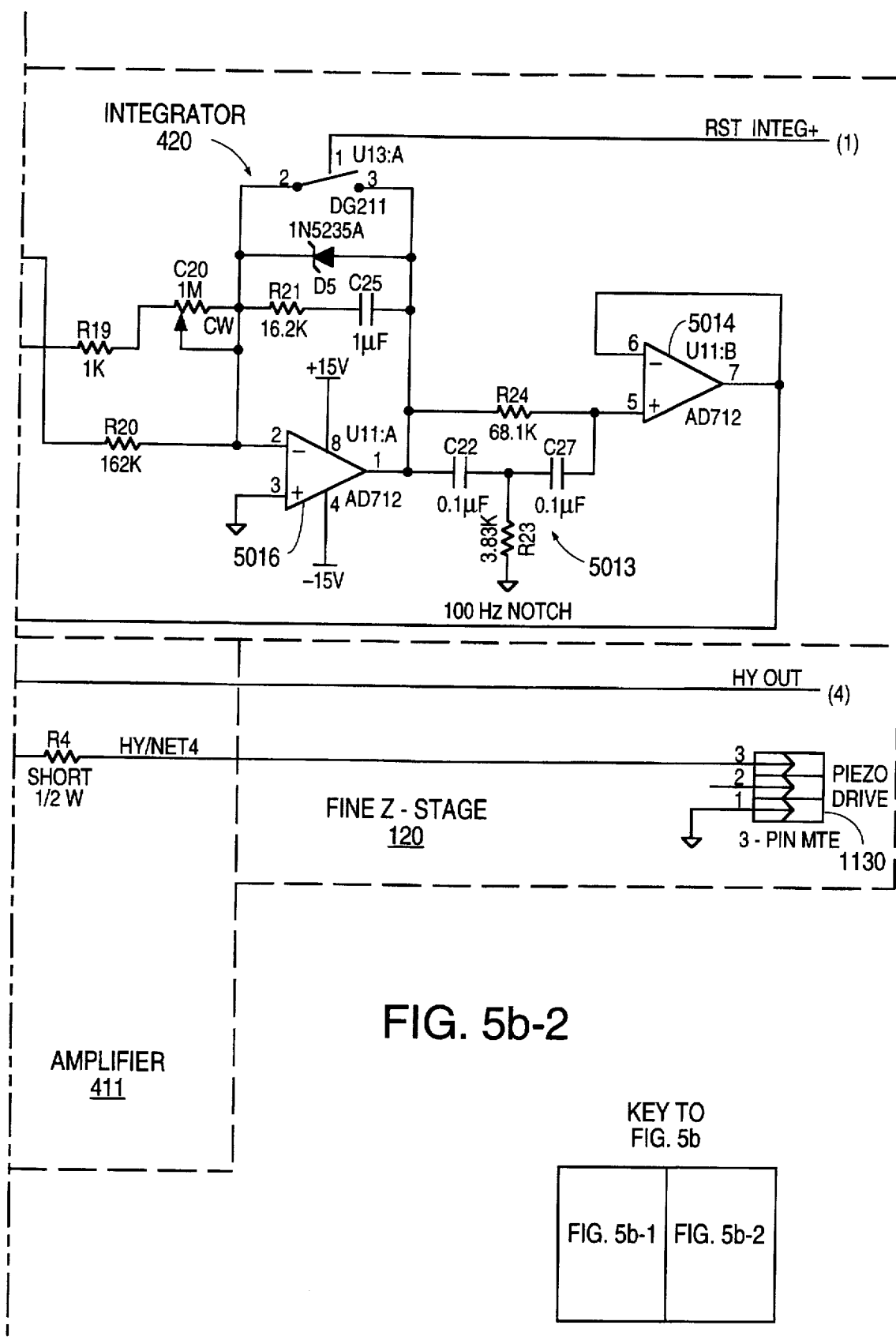
Figures 1, 5C:
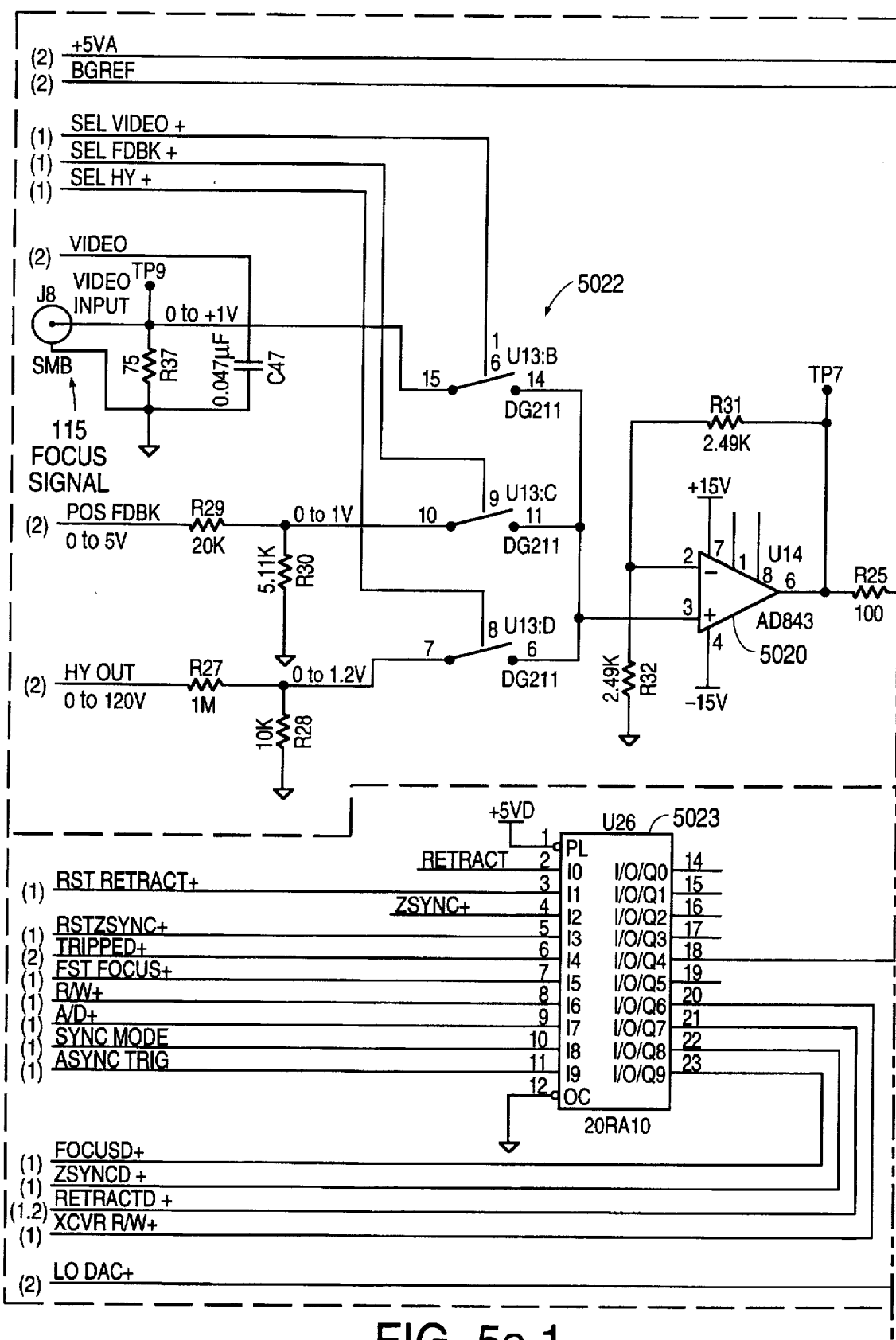
Figures 2, 5C:
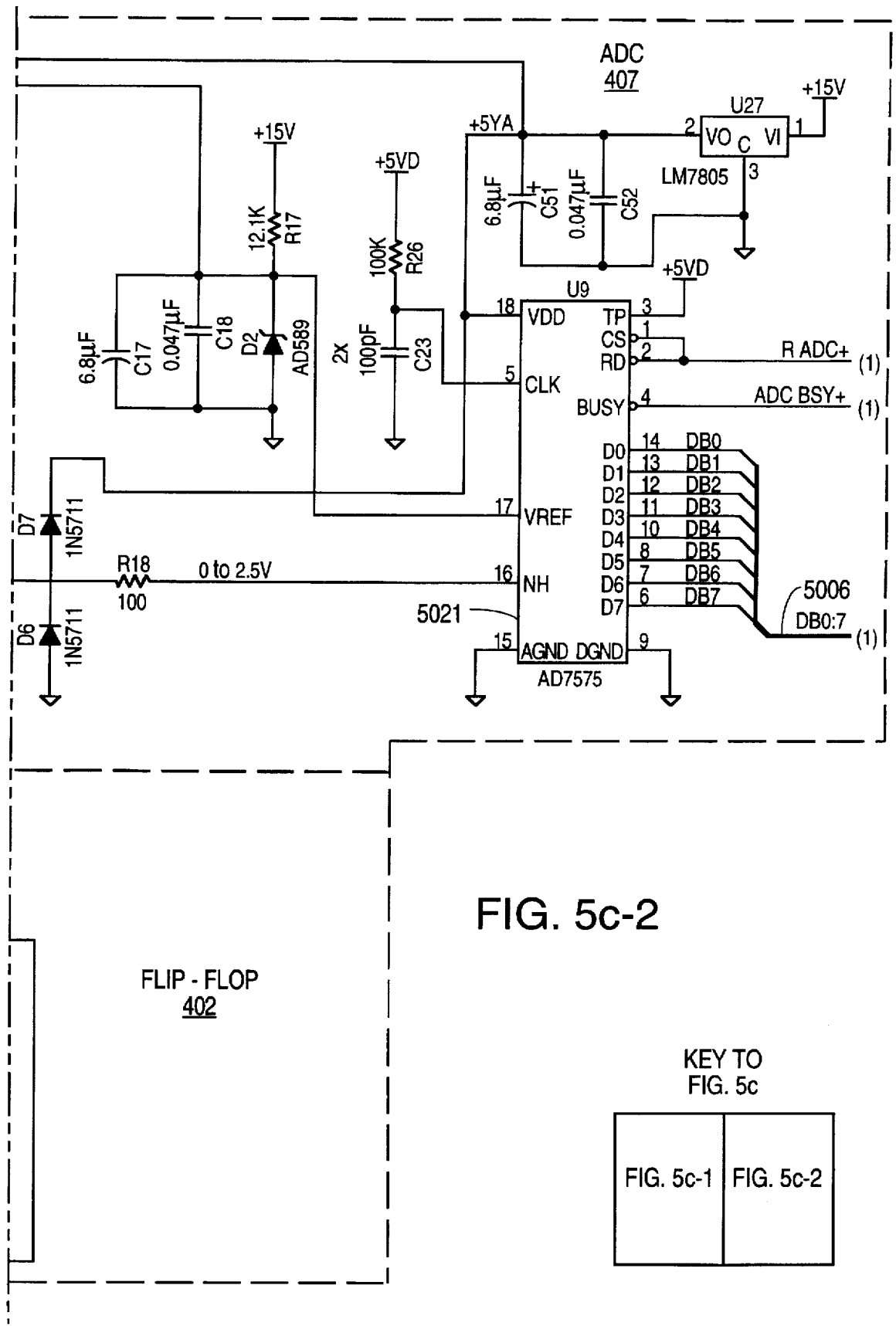
Figures 1, 5D:
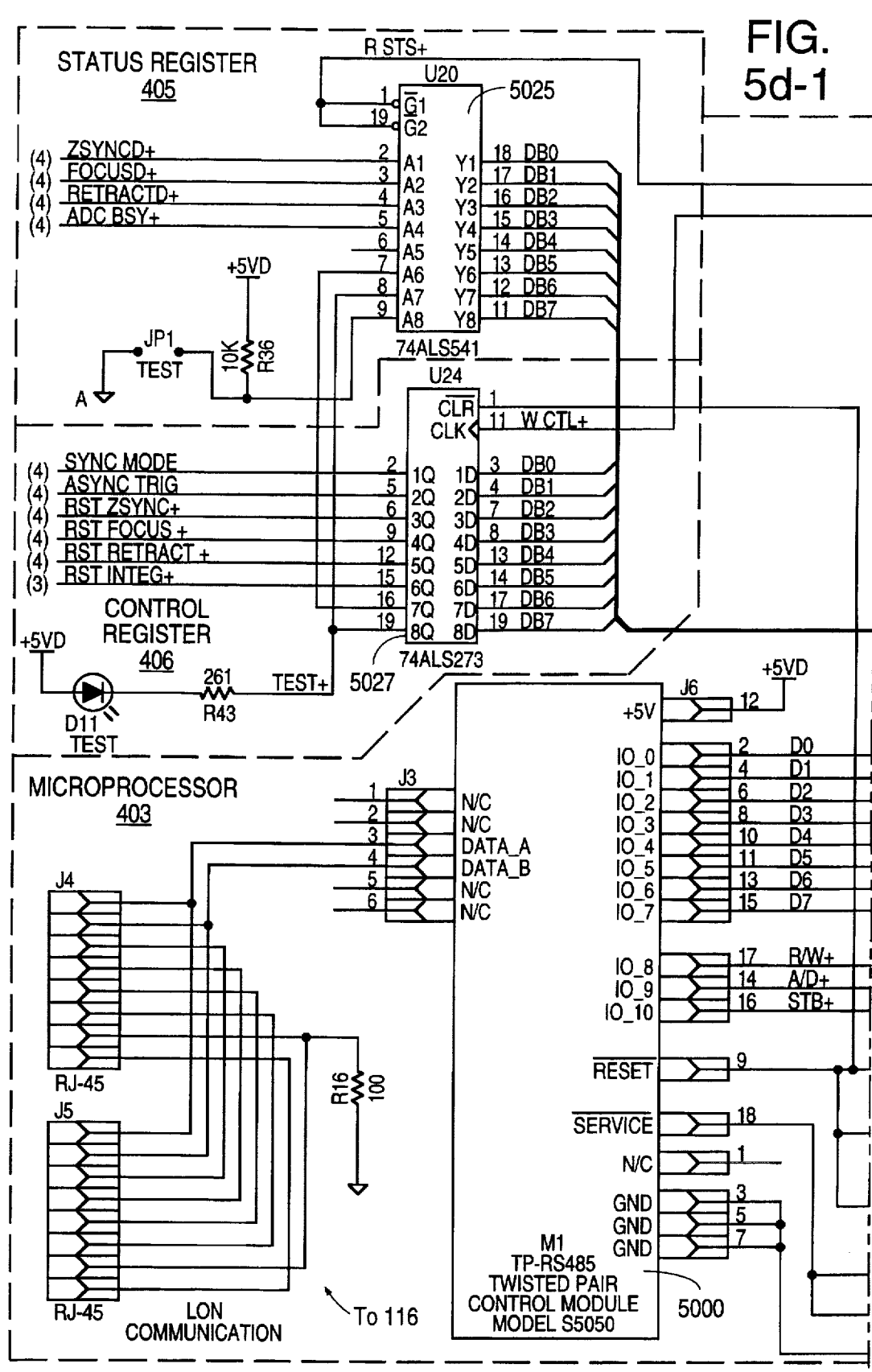
Figures 2, 5D:
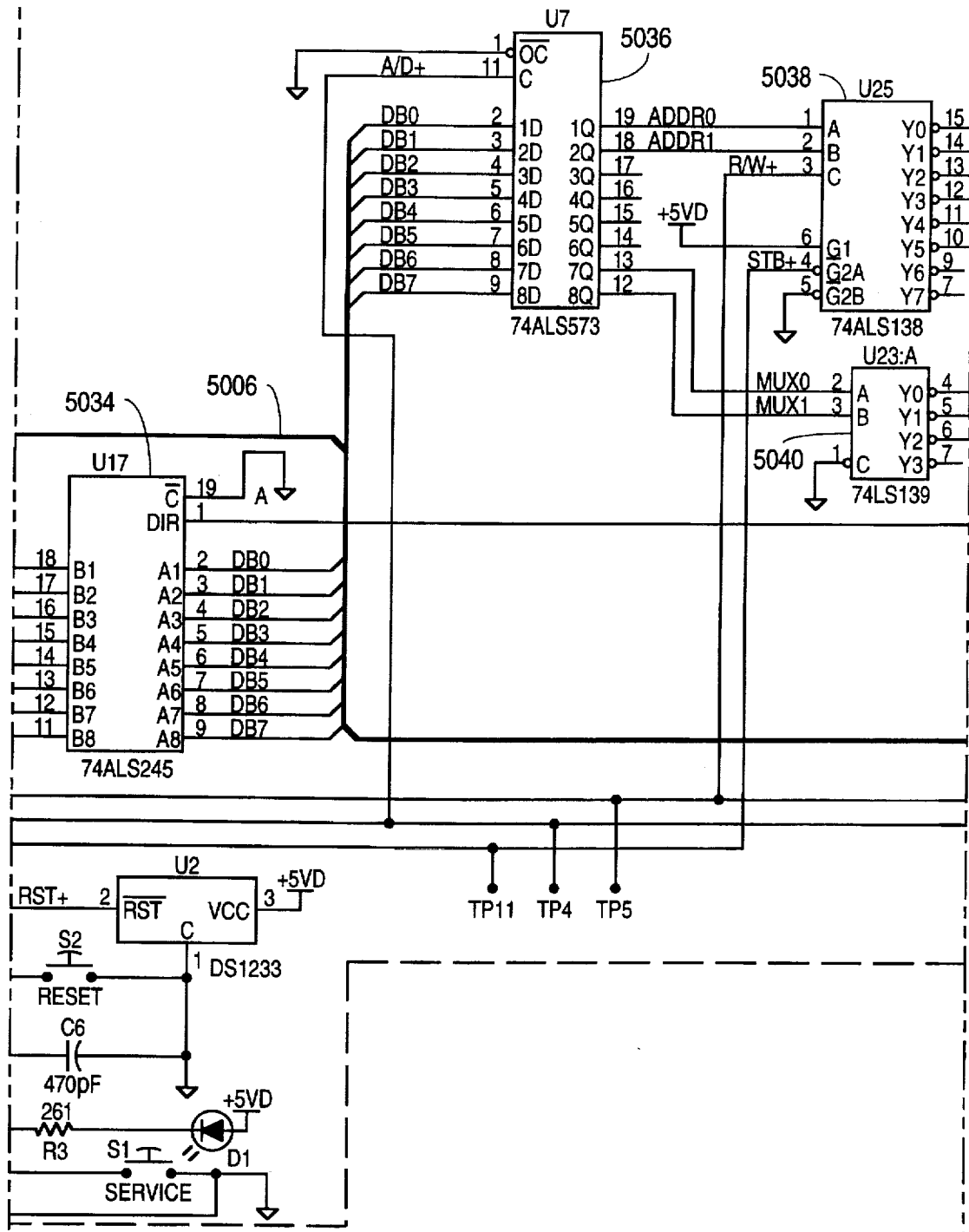
Figures 3, 5D:
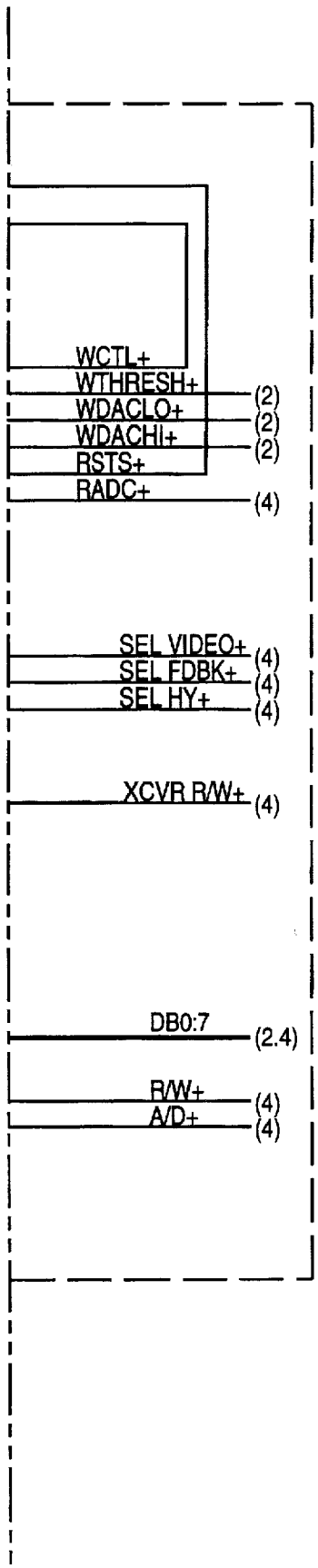

FIGS. 5a–5e are schematic diagrams of the Z-axis controller 118 of FIG. 4. Similar elements in FIGS. 4 and 5a–5e are labelled with the same number. As shown in FIG. 5d, central processing unit (CPU) 5000 of microprocessor 403 transmits and receives information through bus transceiver 5034 to 8-bit data bus 5006. CPU 5000 is a TP-RS485 twisted-pair control module, model number 55050-00, available from Echelon. Bus transceiver 5034 provides additional drive capability to CPU 5000.

Bus transceiver 5034 is a well-known device, available as part number 74ALS245, from Texas Instruments (TI). When the microprocessor 403 attempts to access a particular device within the Z-axis controller 118, the CPU 5000 sends address information corresponding to that device to address register 5036 through bus transceiver 5034 and over data bus 5006. (Address register 5036 is available from TI as part number 74ALS573.) The output signal of address register 5036 is provided to address decoders 5038 and 5040, which decode the output signal and generate control signals to the device being accessed. For example, if the CPU 5000 sent address information directed to enabling the input of video data, address decoder 5040 would output a logic zero on SEL_VIDEO*, thereby closing video input switch 5022 of FIG. 5c. Address decoders 5038 and 5040 are available from TI as part numbers 74ALS138 and 74LS139, respectively.

Microprocessor 403 communicates with position control register 408, status register 405, control register 406, DAC 404 and ADC 407 using 8-bit data bus 5006.

As shown in FIG. 5a, registers 5001 and 5003 within position control register 408 receive positioning information from microprocessor 403 on data bus 5006. Registers 5001–5004 are known in the art. Registers 5001 and 5003, available from TI as part number 74ALS574, serve as buffer registers that, when clocked, make the eight-bit data word on data bus 5006 available as input to registers 5002 and 5004. Registers 5002 and 5004, available from TI as part number 74ALS273, serve as storage registers that, when clocked by the signal LD_DAC*, store the eight-bit data words output by registers 5001 and 5003 and apply these data words to the input of 12-bit DAC unit 5008 of DAC 409. DAC unit 5008 is a conventional DAC, known in the art, and available from Analog Devices as part number AD7541. The remaining ancillary elements of DAC 409 (including operational amplifier 5009 and the illustrated resistors, capacitors, and diodes) are conventional elements known in the art. Operational amplifier 5009 is available from Analog Devices as part number OP-177E. DAC 409 provides an analog output signal on lead 5010.

As shown in FIG. 5b, lead 5010 is connected to one input of operational amplifier 5012 of summing node 410. Operational amplifier 5012 is available as part number AD712 from Analog Devices. The other input to operational amplifier 5012 is derived from the position feedback signal provided by a position sensor (not shown) in fine Z-stage 120 with an output coupled to a connector 1135. Operational amplifier 5018 is available from Analog Devices as part number AD712. Operational amplifier 5018 an its associated resistors and capacitors are configured as a conventional buffer.

The output signal from operational amplifier 5018 is provided to the inverting input of operational amplifier 5012. The output signal from summing node 410 is coupled to the input of a conventional integrator 420, which includes an operational amplifier 5016, such as part number AD712 available from AD, and associated elements.

The output signal from integrator 420 is provided to notch filter 5013, which includes two resistors and two capacitors. The output signal from notch filter 5013 is provided to operational amplifier 5014, which is available from Analog Devices as part number ad712. The output signal from operational amplifier 5014 is provided to the input of amplifier 411.

Amplifier 411 is a conventional amplifier that includes an operational amplifier available from Apex as part number PA85. The combination of diodes, resistors, and capacitors associated with amplifier 411 are all known in the art. The output signal from amplifier 411 is provided through a connector 1130 to a piezoelectric element (not shown) within the fine Z-stage 120.

As shown in FIG. 5c, the electric focus signal on lead 115 is provided to ADC 407. The electronic focus signal on lead 115 is routed through multiplexer 5022 to operational amplifier 5020. Multiplexer 5022 is a conventional part available from Siliconix as part number DG 211. Operational amplifier 5020, available from Analog Devices as part number AD843, buffers the electric focus signal on lead 115. The output signal from operational amplifier 5020 is provided to an input of ADC unit 5021. ADC unit 5021 is a conventional part available as part number AD7575 from Analog Devices. The other devices coupled to ADC unit 5021, as illustrated in FIG. 5c, are known in the art. In response to the electric focus signal on lead 115, ADC unit 5021 outputs an 8-bit digital signal representative of the electric focus signal on lead 115. The 8-bit digital output signal of ADC unit 5021 is provided to microprocessor 403 on data bus 5006.

FIG. 5c also illustrates flip-flop 402. Flip-flop 402 is programmed as one of the devices present within programmable logic device (PLD) 5023. PLD 5023 is available from Lattice Semiconductor as part number GAL20RA10. The inputs to PLD 5023 include a set input from comparator 401 and a reset input from control register 406. PLD 5023 processes these inputs and generates an output representing the Q output signal from flip-flop 402. This Q output is provided to status register 405. (PLD 5023 also has inputs and outputs unrelated to automatic focus operations.)

FIG. 5d illustrates status register 405, which is a conventional register available as part number 74ALS541 from TI. As previously discussed, status register 405 receives the Q output signal from flip-flop 402. (Status register 405 also receives other information unrelated to automatic focus operations.) The 8-bit output signal from status register 405 is provided to data bus 5006 such that microprocessor 403 can detect when flip-flop 402 sets.

Control register 406 (FIG. 5d) receives an 8-bit input from microprocessor 403 on data bus 5006. Control register 406 is available from TI as part number 74ALS273. An output signal from control register 406 is coupled to PLD 5023, such that a signal from control register 406 can reset flip-flop 402.

Referring again to FIG. 5a, DAC 404 also receives an 8-bit input from microprocessor 403 on data bus 5006. This 8-bit input is transmitted through register 5007 (available from TI as part number 74ALS574) to conventional DAC unit 5011 (available from National Semiconductor as part number DAC0808). DAC unit 5011 converts the incoming 8-bit signal to an analog output signal. This analog output signal is provided to an input of operational amplifier 5017 (available from Analog Devices as part number AD712). The output signal from operational amplifier 5017 is provided to an input of comparator 401. The electric focus signal is provided to the other input of comparator 401. Comparator 401 includes comparator unit 5019, available from National Semiconductor as part number LM311. The output signal from comparator 401 is provided to flip-flop 402.

Figures 1, 5E:
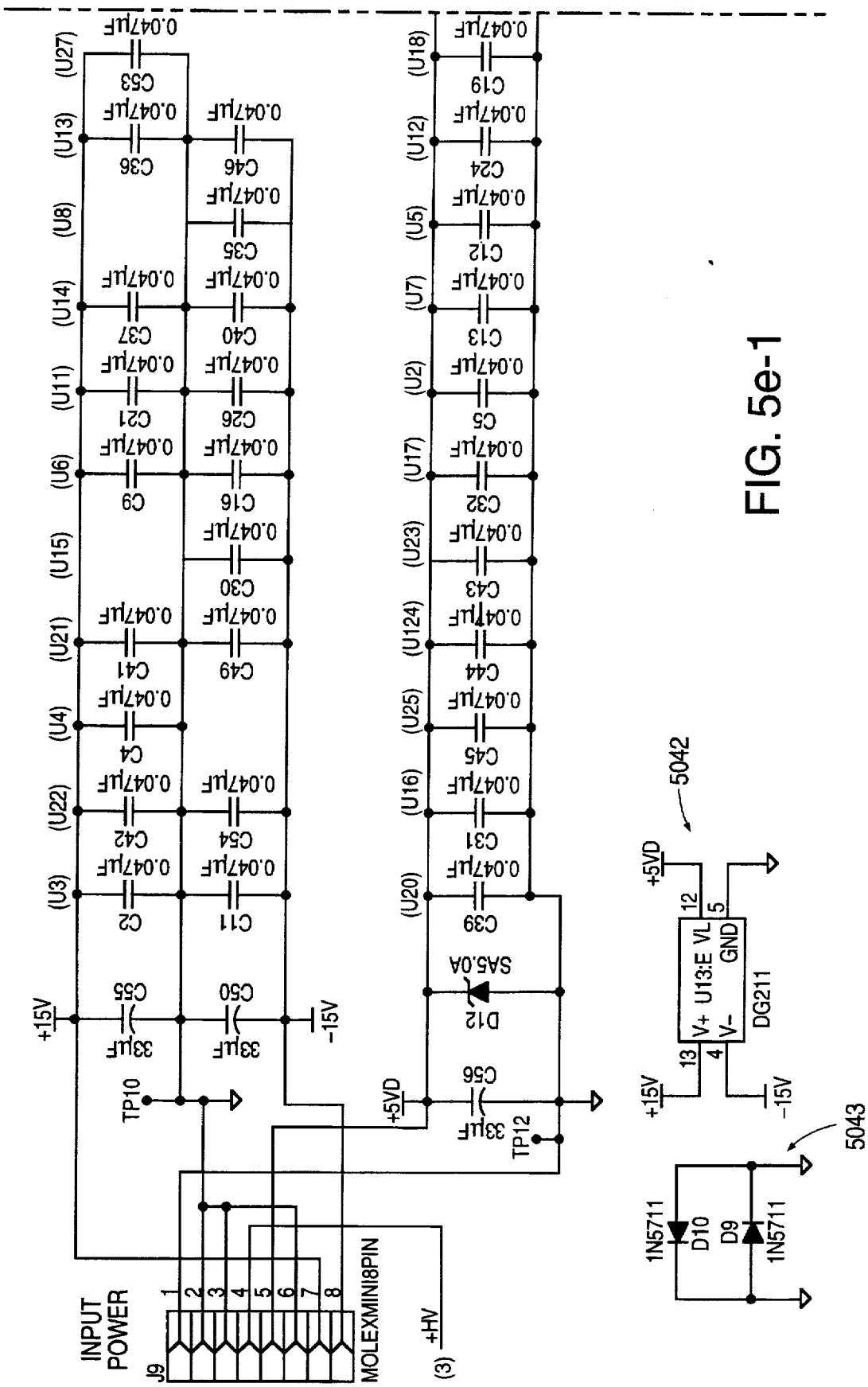

FIG. 5e illustrates the power supply connections 5041, 5042 and analog/digital grounding structure 5043 for Z-stage controller 118.

Figure 6A:
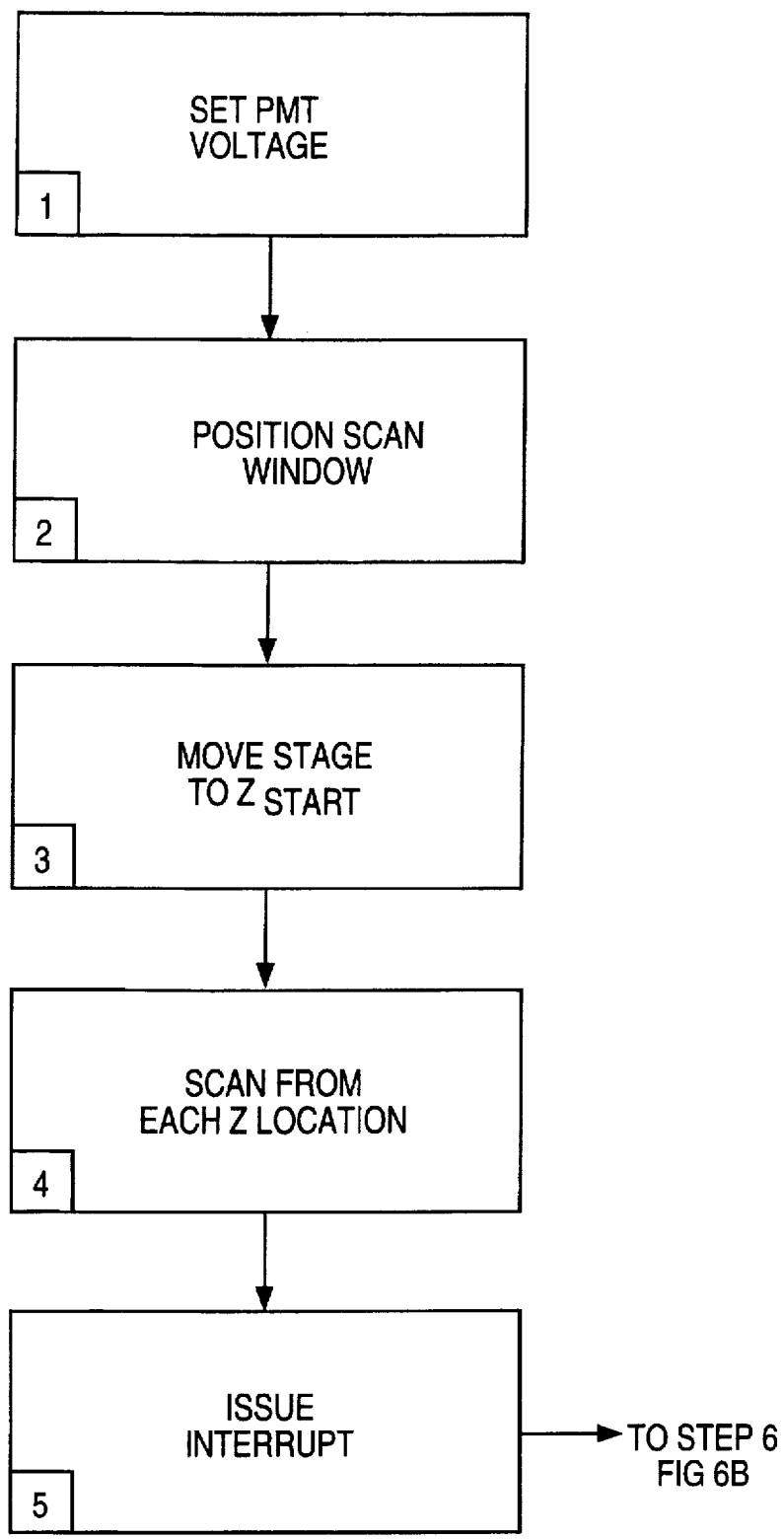
FIGS. 6A and 6B describe the process of obtaining surface information with which to determine and set the scan parameters appropriate for a particular sample.
Figure 6B:
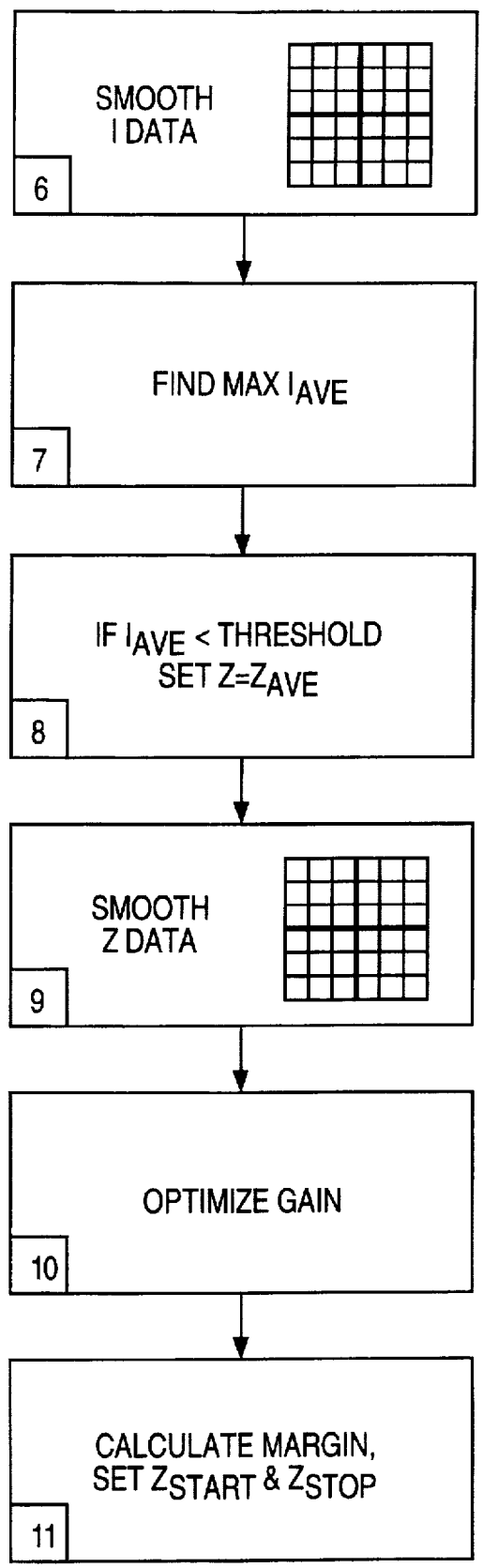

FIGS. 6A and 6B describe the process of obtaining surface information with which to determine and set the scan parameters appropriate for a particular target 112. In one embodiment, a user instigates this process by selecting a "SetZ" button. For example, the SetZ button may be an icon on a computer screen associated with host work station 116, or the SetZ function may be assigned to a function key.

The computer code used to perform a SetZ operation in accordance with an embodiment of the present invention is set forth in the Appendix. The computer code of the Appendix is written in C, a well-known programming language.

Beginning at step 1 of FIG. 6A, the gain of photodetector 114, and hence the measured intensity of laser beam 123 reflected from target 112, is grossly adjusted. In one embodiment, for example, photodetector 114 is a photo-multiplier tube (PMT) that includes a gain terminal 114A. The gain of the PMT is adjusted by changing the voltage on gain terminal 114A. In one embodiment, a digital-to-analog converter (not shown) is coupled between work station 116 and gain terminal 114A so that the gain of photodetector 114A may be set by supplying an appropriate digital input to the digital-to-analog converter.

In step 1, the input voltage on gain terminal 114A is compared to a pre-determined upper limit. If the gain voltage is greater than this upper limit, the gain voltage is set to the upper limit. If, on the other hand, the gain voltage is less than a predetermined lower limit, the gain voltage is set to the lower limit. The upper limit is selected to ensure that a reflected surface image does not saturate the photodetector 114, the lower limit to avoid errors due to a low signal-to-noise ratio. Finally, if the gain voltage is within the established limits, the gain voltage is left alone.

As shown FIG. 6A, once the gain voltage on gain terminal 114A is set within the established limits, system 100 moves to step 2 of FIG. 6A, in which system 100 determines the Z range over which to scan target 112. The range of motion of fine Z-stage 120 is, in one embodiment, 50 microns. That is, host work station 116, through Z-axis controller 118, can direct fine Z-stage 120 to move vertically to cover a total distance of up to 50 microns. However, wafer features are typically much smaller than 50 microns, so a 50 micron SetZ scan would be unnecessarily large. Therefore, the SetZ scan range (i.e., the "scan window") is normally configured to be something less than 50 microns. A typical scan window is, for example, 25 microns.

The scan window is normally centered on focus position 203, so the start point of the scan ("$Z_{start}$") is determined by adding half of the predetermined Z scan range to focus position 203, and the stop point of the scan ("$Z_{stop}$") is determined by subtracting half of the predetermined Z scan range from focus position 203.

When focus position 203 plus half the scan range is above the maximum Z height attainable with fine Z-stage 120 ("$Z_{max}$"), $Z_{start}$ is set to $Z_{max}$ and $Z_{stop}$ is set to $Z_{max}$ minus the scan range. Similarly, when focus position 203 minus half the scan range is below the minimum Z height attainable with fine Z-stage 120 ("$Z_{min}$"), $Z_{stop}$ is set to $Z_{min}$ and $Z_{start}$ is set to $Z_{min}$ plus the scan range.

In one embodiment, an automatic focus operation may be performed prior to step 2 to determine the approximate focus position 203 of the sample surface within the coarse scan range of the microscope. The autofocus operation is generally not required in the SetZ sequence shown, as an autofocus is normally performed prior to the SetZ operation. Furthermore, once an autofocus is performed on one portion of a relatively flat target, such as a semiconductor wafer, it is generally unnecessary to perform subsequent autofocus operations for other points on that target. In such cases, the automatic focus operation is not performed more than once because it wastes valuable time. For a more detailed description of automatic focusing, see the commonly owned application entitled "A Method and Apparatus for Performing an Automatic Focus Operation," the content of which is incorporated herein by reference.

As shown in steps 3 and 4 of FIG. 6A, once host work station 116 obtains the $Z_{start}$ and $Z_{stop}$ positions, host work station 116 directs Z-axis controller 118 to move fine Z-stage 120 to the $Z_{start}$ position. System 100 then begins a series of scans of the surface of target 112, moving step-by-step toward $Z_{stop}$, to acquire a slice of data values for each Z position.

As system 100 scans the surface of target 112 from each Z position, the maximum reflected intensity and Z location corresponding to the maximum reflected intensity are determined for each point (X-Y coordinate) on the surface of target 112. This information is used to create an array of maximum intensity values and an array of Z values corresponding to the location along the Z axis of each of the maximum intensity values.

In one embodiment, each intensity value of each slice of intensity data is compared to a maximum intensity value corresponding to the same X-Y coordinate in the array of maximum intensity values. If the intensity value of the slice is greater than the corresponding maximum intensity value, then the intensity value of the array of maximum intensity values is updated with a new maximum intensity value for that X-Y coordinate and the array of Z values is updated with the Z location of the new maximum intensity value. Because the point of maximum reflected intensity gives an indication of the location of the surface, the array of Z values provides an indication of the surface contour.

In a second embodiment, the maximum reflected intensity and Z location associated with the maximum reflected intensity for a particular point on the surface may be determined by comparing each data value associated with that point after slices of data are obtained and stored for all Z locations. This second method is slower and requires more memory than the first, as it is necessary to store all of the data values for each slice.

For a more detailed description of confocal microscope surface extraction techniques, see the copending application entitled "Surface Extraction from a Three-Dimensional Data Set," the content of which is incorporated herein by reference.

As shown in step 5 of FIG. 6A, upon completion of the surface scan, fine Z-stage 120 issues an interrupt signal to work station 116, indicating that the data acquisition is complete.

The number of steps in a SetZ scan is user-configurable. Generally, a greater number of steps provides for better image resolution along the Z axis. Unfortunately, each scan step takes time. For this reason, the number of steps (i.e., the number of "slices" of surface data) is limited. Moreover, the minimum step size is limited by the resolution of the microscope. For example, in the embodiment described in connection with FIG. 3, the half-max measurement 305 of 0.5 microns limits the resolution of the microscope in the Z direction such that providing a step size of less than 0.5 microns will not further increase resolution. For the foregoing reasons, one embodiment uses 50 steps over a scan range of 25 microns, yielding a step size of 0.5 microns.

In step 6, host work station 116 smooths the intensity data stored in the array of maximum intensity values by, for example, averaging the intensity values for a number of neighboring X-Y locations. In one embodiment, the work station 116 divides the X-Y locations into groups of nine (i.e., a three-by-three grid of X-Y locations) and assigns each group an average intensity value $I_{ave}$ equal to the average of the maximum intensity values corresponding to the X-Y locations in that group. This smoothing minimizes the effects of noise on the intensity data.

In step 7 of FIG. 6B, host work station 116 compares each $I_{ave}$ value to the others to obtain the maximum $I_{ave}$. Then, in step 8, each $I_{ave}$ value is compared to a minimum-intensity threshold value to determine whether the resulting Z value for that group of pixels may be trusted. The minimum-intensity threshold value is established using the minimum and maximum $I_{ave}$ values. For example, in an embodiment that uses an intensity scale of from 0 to 255 to determine the PMT voltage on gain terminal 114A, the minimum-intensity threshold is established using the equation:

$$\text{MinimumThreshold} = MinI_{ave} + 8 + (MaxI_{ave} - MinI_{ave})/16$$

where $MinI_{ave}$ is the minimum average intensity value and $MaxI_{ave}$ is the maximum average intensity value.

If the reflected intensity is too low, the resulting Z value may be erroneous due to a relatively low signal-to-noise ratio. For this reason, the Z values associated with X-Y locations having $I_{ave}$ values below the minimum threshold are set to the average Z value (i.e., the average feature height) for target 112. This function reduces the effects of noise on the Z values used to set the scan parameters.

In step 9, host work station 116 smooths the data stored in the array of Z values by, for example, averaging the Z values for a number of neighboring X-Y locations. In one embodiment, work station 116 divides the X-Y locations into groups of nine (i.e., a three-by-three grid of X-Y locations, wherein each X-Y location has a corresponding Z value) and assigns each group an average Z value $Z_{ave}$ equal to the average of the Z values corresponding to the X-Y locations in that group. This smoothing minimizes the effects of noise on the Z data.

Next, in step 10, work station 116 optimizes the gain of photodetector 114 by adjusting the voltage on gain terminal 114A. The maximum $I_{ave}$ value ("$I_{ave\_max}$") is compared to a predetermined ideal maximum intensity value. If the maximum $I_{ave}$ is less than the ideal value, then the gain of photodetector 114 is increased. If, on the other hand, the maximum $I_{ave}$ is greater than the ideal value, then the gain of photodetector 114 is decreased. In the embodiment that uses a Hamamatsu R268 PMT, the gain may be set to provide a desired maximum output level on lead 115 using the equation:

$$\Delta\text{Gain} \approx 9 \times \frac{\log (\text{Ideal } I)}{\log (I_{ave\_max})}$$

where "Ideal I" is the desired maximum measured intensity output from PMT 114. The resulting ΔGain is added to the current digital gain setting input to the digital-to-analog converter (not shown) coupled between work station 116 and gain terminal 114A. Of course, other types of photodetectors could be used that have different relationships between input voltage and intensity, in which case it would be necessary to determine the relationship between the gain and the input voltage to properly set the gain.

Finally, in step 11, the maximum measured Z value ("$Z_M$") and the minimum measured Z value ("$Z_m$") are used to calculate a safety margin $S_M$ for a subsequent scan. This safety margin is added to $Z_M$ and subtracted from $Z_m$ to determine the start and end points, respectively, of the next scan. In other words, $Z_{start} = Z_M + S_M$, and $Z_{stop} = Z_m - S_M$.

Many different methods may be used to calculate an appropriate safety margin $S_M$. In one embodiment, for example, the safety margin $S_M$ is equal to 2.5 microns plus 20% of the difference between $Z_M$ and $Z_m$ (i.e., $S_M = 2.5$ microns $+ 0.2(Z_M - Z_m)$).

The microscope may be configured to perform a number of different actions after establishing the appropriate Z-scan and photodetector gain settings. For example, the host work station 116 may prompt the user for further instructions, or may scan the surface from $Z_{start}$ to $Z_{end}$, dividing the distance between $Z_{start}$ and $Z_{end}$ into the preconfigured number of steps (e.g., 50 steps), thereby generating a three-dimensional set of data values. System 100 can then extract a surface image of target 112 from this three-dimensional set of data values. (One method of performing such an extraction is detailed in the co-pending application entitled "Surface Extraction from a Three-Dimensional Data Set," the content of which is incorporated herein by reference.)

While the present invention has been described in connection with specific embodiments, variations of these embodiments will be obvious to those having ordinary skill in the art. For example, although the present invention was described in connection a particular auto-focus scheme, other auto-focus schemes are available to provide the location of target 112. Additionally, while the invention is described in connection with microscope that reflects a maximum intensity to the photodetector during a focused condition, it is clear that the invention may be modified to operate with a microscope that reflects a minimum intensity to the photodetector during a focused condition. Therefore, the spirit and scope of the appended claims should not be limited to the description of the preferred versions.

APPENDIX

Ultrapointe Corporation, copyright 1994.
All rights reserved.

L:\DMS\8772\M-2466_U\0119119.03
(AJB)

```
/************************************************
 * (c) copyright Ultrapointe, 1994
 * All rights reserved
 *
 * zrange.c
 * handles the setting of Z scan range/intensity
 ************************************************
 */
#ifdef Irix5plus
#define NeedFunctionPrototypes 1
#else
#define FUNCPROTO
endif include <stdio.h>
include <stdlib.h>
#include <math.h>
#include <X11/Intrinsic.h>
include <Xm/Xm.h> include "uv_util.h"
include "wfrfile.h"
#include "uv_data.h"
#include "xw_util.h"
#include "uvconfig.h"
#include "ulsdp.h"
#include "sdp.h"
#include "confocal.h"
#include "Ionuiimg.h"
#include "zrange.h"

define SEARCH_STEP_SIZE    30 static BOOL zrGetZSmoothedTo16( BYTE *pZ, int iDim, float *fMaxZ, float *fMinZ);
static BOOL zrGetIntensitySmoothedTo16( BYTE *pZ, int iDim, float *fMaxZ, float *fMinZ,
                                        int *iMaxXPos, int *iMaxYPos);
static BOOL zrPeakFitGetMaxMin( BYTE *pZ, int iDim, int iMaxXPos, int iMaxYPos,
                                float *fMaxZ );
static BOOL zrValidateStartEndNewZ( int *iStartZ, int *iEndZ, int *iNewZ);
static BOOL zrNoiseFilterZ( BYTE *pZ, BYTE *pI, int iDim, float fMaxI, float fMinI);

extern BOOL SetZ(Widget w, SDP_DATA_ACQ_MODE eImgType)
    {
    BOOL            rt = TRUE;
    int             iNumSlice, iStepSize;

zr_SetupToStartZRangeAcq( &iNumSlice, &iStepSize);
    UVData.Lon.eSDPAcq = eImgType;
    rt = Ionui_TakeNewVolumeOrSurface(w, &UVData.Lon, iNumSlice, iStepSize);
```

```
    return rt;
}
/*********************************************************
 * Initialize step size, num slices and move Z stage
 * setup to do a set range surface acq
 * 1: lower laser intensity, to make sure resultant image
 *                will not saturate. If it does, we dont know
 *                how much to adjust.
 * 2: move fineZup half search range
 * 3: wait .1 second for fineZ to settle/ PMT to settle.
 *
 *********************************************************
 */
#define SETZ_LASER_I_SETBACK      18
extern BOOL zr_SetupToStartZRangeAcq( int *iNumSlice, int *iStepSize)
{
int          iNewLaserI, iCurrZ, iStartZ, iEndZ;
UV_CONFIG *pCfg  = cfg_GetLockRdConfig();
UI_LON_IMAGE    *pUIImg = Ionui_GetLonUiImg();

iNewLaserI = pUIImg->LaserPwr;
if( pUIImg->LaserPwr < 5)
   iNewLaserI = 5;
if( pUIImg->LaserPwr > SETZ_LASER_I_SETBACK)
   iNewLaserI = SETZ_LASER_I_SETBACK +
              ( (pUIImg->LaserPwr - SETZ_LASER_I_SETBACK) /2 );
if( iNewLaserI != pUIImg->LaserPwr)
   Ionui_LaserPwrAndPMT( iNewLaserI);

*iNumSlice = pCfg->SysSpec.ZRangeNumSteps;
iCurrZ = Ionui_GetCommandedFastZPos();
iStartZ= iCurrZ + ( (SEARCH_STEP_SIZE * *iNumSlice)/2);
if( iStartZ > 4095)
   iStartZ = 4095;
iEndZ = iStartZ - ( SEARCH_STEP_SIZE * *iNumSlice);
if(iEndZ < 0)
      iEndZ = 0;
*iStepSize = ( iStartZ - iEndZ) / *iNumSlice;
Ionui_SetFastZPos( iStartZ);
util_sginap( 10);
return TRUE;
}

/*********************************************************
 * read surface and set z scan range
 * The array of Z's is first filtered:
 *       1, Any Z values with its corresponding Intensity less
 *              than threshold is set to the averge height(z)
 *       2, Threshold is calculated to be some value above minimum
 *
 *********************************************************
 */
extern BOOL zr_ReadSurfAndSetRange( OPTICS_PARMS *pScan, int CurrZ )
```

```
{
UI_LON_IMAGE *pUIImg = Ionui_GetLonUiImg();
UV_CONFIG *pCfg    = cfg_GetLockRdConfig();
BYTE       *pI, *pZ;
int        iStepSize,iStartZ, iNewZ, iEndZ, MaxXPos, MaxYPos;
double dExtRange;
float  fMaxZ, fMinZ, fMaxI, fMinI, fNewZ;
BOOL       rt = FALSE;

iEndZ = CurrZ - ( SEARCH_STEP_SIZE * pCfg->SysSpec.ZRangeNumSteps);
if(iEndZ < 0)
  iEndZ = 0;
iStepSize = ( CurrZ - iEndZ) / pCfg->SysSpec.ZRangeNumSteps;

pI = (BYTE *)XtMalloc( MAX_ARRAY_SIZE);
pZ = (BYTE *)XtMalloc( MAX_ARRAY_SIZE);

rt = sdp_ReadSurfaceFrSDP( pScan->YDim, pScan->YDim, (char *)pI,(char *)pZ);
if( rt == TRUE)
   {
   zrGetIntensitySmoothedTo16( pI, pScan->YDim, &fMaxI, &fMinI,
                                                   &MaxXPos, &MaxYPos);
   zrPeakFitGetMaxMin( pZ, pScan->YDim, MaxXPos, MaxYPos, &fNewZ);
   zrNoiseFilterZ       ( pZ, pI, pScan->YDim, fMaxI, fMinI);
   zrGetZSmoothedTo16( pZ, pScan->YDim, &fMaxZ, &fMinZ);

dExtRange = 2.5 + abs(((double)fMaxZ - fMinZ) * 0.2);

iStartZ = CurrZ - ( ( fMinZ - dExtRange) * iStepSize);
   iEndZ   = CurrZ - ( ( fMaxZ + dExtRange) * iStepSize);
   iNewZ   = CurrZ - ( (double)fNewZ * iStepSize);
   zrValidateStartEndNewZ( &iStartZ, &iEndZ, &iNewZ);
   lonui_SetFastZPos( iNewZ);
   zr_SetTargetLaserIFrImgInten( (int)fMaxI, pUIImg->LaserPwr);
   pScan->StepSize = ((iStartZ - iEndZ)/ pScan->NumSlice) + 1;
   pScan->StartZStepOffset = iStartZ - iNewZ;
   }
XtFree((char *) pI);
XtFree((char *) pZ);
return rt;
}
/***********************************************************
* noise filter Z
***********************************************************
*/
static BOOL zrNoiseFilterZ( BYTE *pZ, BYTE *pI, int iDim, float fMaxI, float fMinI)
{
int    iCt, iSize, iAvg, iSum, iThres;

iSize = iDim * iDim;
for( iSum = 0, iCt = 0; iCt< iSize; iCt++)
  iSum = (int)pZ[iCt] + iSum;
iAvg = iSum / iSize;
iThres = fMinI + 8.0 + ( (double)fMaxI - fMinI)/16;
```

```c
    for( iCt = 0; iCt< iSize; iCt++)
      {
      if( (int)pI[iCt] < iThres)
          pZ[iCt] = iAvg;
      }
    return TRUE;
    }

/****************************************************
 * validate z scan positions: start, end, new
 * min spacing 64( 64 slices , stepsize of 1)
 ****************************************************
 */
#define MIN_SEPERATION      64
#define NEW_POS_RANGE      .35
static BOOL zrValidateStartEndNewZ( int *iStartZ, int *iEndZ, int *iNewZ)
  {
  int    iLimit;

if( *iStartZ > 4095)
     *iStartZ = 4095;
  if( *iStartZ < MIN_SEPERATION)
     *iStartZ = MIN_SEPERATION;
  if( *iEndZ > ( *iStartZ - MIN_SEPERATION) )
     *iEndZ = *iStartZ - MIN_SEPERATION;
  if( *iEndZ < 0)
     *iEndZ= 0;
  iLimit = ( *iStartZ - *iEndZ) * NEW_POS_RANGE;
  if( *iNewZ < (*iEndZ + iLimit) )
     *iNewZ = *iEndZ + iLimit;
  if( *iNewZ > (*iStartZ - iLimit) )
     *iNewZ = *iStartZ - iLimit;
  return TRUE;
  }

/****************************************************
 * conbine every 4x4 to 1
 ****************************************************
 */
#define SMOOTH_SKIP_FACTOR 3
static BOOL zrGetIntensitySmoothedTo16( BYTE *pZ, int iDim, float *fMaxZ, float *fMinZ,
                                        int *iMaxXPos, int *iMaxYPos)
  {
  int     iXCt, iYCt;
  BYTE    *pTmp;
  int     i2Dim, iLimit;
  int     iMin, iMax, iMinXPos, iMinYPos;
  int     iTmp, iLocMaxXPos, iLocMaxYPos, iLocMinXPos, iLocMinYPos;

iMin   = 9 * 255;
  iMax   = 0;
  i2Dim  = iDim + iDim;
  *iMaxXPos = 0;
```

```
*iMaxYPos = 0;
iMinXPos = 0;
iMinYPos = 0;

iLimit = iDim - SMOOTH_SKIP_FACTOR + 1;
for( iYCt=0; iYCt < iLimit; iYCt += SMOOTH_SKIP_FACTOR)
  {
  pTmp = &(pZ[ iYCt * iDim]);
  for( iXCt= 0; iXCt < iLimit; iXCt += SMOOTH_SKIP_FACTOR)
      {
      iTmp  = (unsigned)*pTmp + pTmp[iDim] + pTmp[i2Dim]; pTmp++;
      iTmp += (unsigned)*pTmp + pTmp[iDim] + pTmp[i2Dim]; pTmp++;
      iTmp += (unsigned)*pTmp + pTmp[iDim] + pTmp[i2Dim]; pTmp++;
      if( iMax < iTmp)
        {
        *iMaxXPos = iXCt;
        *iMaxYPos = iYCt;
        iMax = iTmp;
        }
      if( iMin > iTmp)
        {
        iMinXPos = iXCt;
        iMinYPos = iYCt;
        iMin = iTmp;
        }
      }
  }
iMax = iMax /9;
iMin = iMin /9;
*fMaxZ = iMax;
*fMinZ = iMin;
if( iMax > 220)            /* if saturated */
   zrPeakFitGetMaxMin( pZ, iDim, *iMaxXPos, *iMaxYPos, fMaxZ );
if( iMin > 3)
   zrPeakFitGetMaxMin( pZ, iDim, iMinXPos, iMinYPos, fMinZ );
return TRUE;
}
/*************************************************************
**************************************************************
*/
static BOOL zrGetZSmoothedTo16( BYTE *pZ, int iDim, float *fMaxZ, float *fMinZ)
  {
  int       iXCt, iYCt;
  BYTE      *pTmp;
  int       i2Dim, i3Dim;
  int       iMin, iMax, iMaxXPos, iMaxYPos, iMinXPos, iMinYPos;
  int       iTmp, iLocMaxXPos, iLocMaxYPos, iLocMinXPos, iLocMinYPos;

iMin    = 16 * 255;
  iMax    = 0;
  i2Dim   = iDim + iDim;
  i3Dim   = i2Dim + iDim;
  iMaxXPos = 0;
  iMaxYPos = 0;
```

```
iMinXPos = 0;
iMinYPos = 0;

for( iYCt=0; iYCt < (iDim -3); iYCt +=4)
   {
   pTmp = &(pZ[ iYCt * iDim]);
   for( iXCt= 0; iXCt < iDim; iXCt+=4)
        {
        iTmp  = (unsigned)*pTmp + pTmp[iDim] + pTmp[i2Dim], pTmp[i3Dim]; pTmp++;
        iTmp += (unsigned)*pTmp + pTmp[iDim] + pTmp[i2Dim], pTmp[i3Dim]; pTmp++;
        iTmp += (unsigned)*pTmp + pTmp[iDim] + pTmp[i2Dim], pTmp[i3Dim]; pTmp++;
        iTmp += (unsigned)*pTmp + pTmp[iDim] + pTmp[i2Dim], pTmp[i3Dim]; pTmp++;
        if( iMax < iTmp)
           {
           iMaxXPos = iXCt;
           iMaxYPos = iYCt;
           iMax = iTmp;
           }
        if( iMin > iTmp)
           {
           iMinXPos = iXCt;
           iMinYPos = iYCt;
           iMin = iTmp;
           }
        }
   }
*fMaxZ = iMax / 16;
*fMinZ = iMin / 16;
if( iMax < (1010 *4) )
   zrPeakFitGetMaxMin( pZ, iDim, iMaxXPos, iMaxYPos, fMaxZ );
if( iMin > 3)
   zrPeakFitGetMaxMin( pZ, iDim, iMinXPos, iMinYPos, fMinZ );
return TRUE;
}

/*********************************************************
* do peak fit to find real peak
* assume iMaxXPos is aligned at 4 data point boundary
*
**********************************************************
*/
static BOOL zrPeakFitGetMaxMin( BYTE *pZ, int iDim, int iMaxXPos, int iMaxYPos,
                                        float *fMaxZ )

{
float    fArray[7];
BYTE     *pTmp;
int      iXStart, iYStart;
int      iCt;
BOOL     rt;

iXStart = iMaxXPos -2;
if( iXStart < 0)
   iXStart = 0;
if( iXStart > (iDim -7))
```

```
   iXStart = iDim -7;

iYStart = iMaxYPos -2;
   if( iYStart < 0)
      iYStart = 0;
   if( iYStart > (iDim -7))
      iYStart = iDim -7;

for( iCt= 0; iCt <7; iCt++)
      {
      pTmp = &( pZ[ (iYStart + iCt) * iDim + iXStart] );
      fArray[iCt] = ((unsigned)pTmp[0] + pTmp[1] + pTmp[2] + pTmp[3] +
                     pTmp[4] + pTmp[5] + pTmp[6]) /7.0;
      }
   rt = util_PeakFit7PtsGetMaxValue( fArray, 7, fMaxZ);
   return rt;
   }
/*********************************************************
* calc new laser intensity based on image intensity
* feedback
* image Intensity here is heavily filtered, and is
* usually lower than actual peak
* if saturated, cut laser intensity by 5
* if less than ideal, incr of 10( maybe in config) laser Inten = 100% img Inten
* for incr of less the 10 laser inten, each step = 10%( linear, not expotenial)
* return TRUE if
**********************************************************
*/
#define IDEAL_IMG_INTEN          195
#define HALF_OF_IDEAL            (IDEAL_IMG_INTEN /2)
define MAX_TARGET_LASER_INTEN   75 extern BOOL zr_SetTargetLaserIFrImgInten( int iImgI, int CurrLaserI)
   {
   UV_CONFIG  *pCfg  = cfg_GetLockRdConfig();
   float   fNew, fCt;
   BOOL       rt = FALSE;
   int        iNewI;

if( iImgI > IDEAL_IMG_INTEN)
      fNew = CurrLaserI - (iImgI - IDEAL_IMG_INTEN) /10;
   else
      {
      fNew = CurrLaserI;
      if( iImgI < 15)
           iImgI = 15;
      for( ; iImgI < HALF_OF_IDEAL; iImgI += iImgI)
           fNew += (double)pCfg->SysSpec.ZRangeLaserGain;
      fCt = (double)pCfg->SysSpec.ZRangeLaserGain * (IDEAL_IMG_INTEN - iImgI) / iImgI;

fNew += (double)fCt;
      if( (int)fNew > MAX_TARGET_LASER_INTEN)
           fNew = MAX_TARGET_LASER_INTEN;
      rt = TRUE;
```

```
        }
    iNewI = fNew;
    if(iNewI < 0)
        iNewI = 0;
    Ionui_LaserPwrAndPMT( iNewI);
fprintf( stderr, "newLI=%d, ", iNewI);
    return TRUE;
    } extern BOOL Ionui_TakeNewVolumeOrSurface( Widget w, OPTICS_PARMS *LonParm,
                                         int NumSlice, int StepSize)

{
    BOOL rt = FALSE;
    int         iMSec;

rt = Ionui_PageScan( LonParm->YDim, LonParm->PixZoom);
    if( rt == TRUE)
        rt = Ion_APICmd( eLonAPIScannerOnOff, SCANNER_STOPDAC | SCANNER_DEFAULT);
    if( rt == TRUE)
        rt = Ion_APICmd( eLonAPIFastZZStep, StepSize) ;
    if( rt == TRUE)
        rt = Ion_APICmd( eLonAPIFastZNumFrames, NumSlice);
    if( rt == TRUE)
        {
        Ionimg_ResetNVUpdatedFlag( FAST_Z_NODE_ADDR, FASTZ_OPSTATUS_NV_ADDR);
        rt = Ion_APICmd( eLonAPIFastZOpMode, FASTZ_OPCMD_SETFORVOL);
        }
    if( rt == TRUE)
        {
        rt = sdp_GenSurface( NumSlice);
        if( rt == TRUE)
            rt = Ion_APICmd( eLonAPIScannerOnOff, SCANNER_DEFAULT);
        if( rt == TRUE)
            {
            iMSec = NumSlice * LonParm->YDim * 1000 / SCANNER_FREQ_HZ;
            iMSec = iMSec * 1.5 * 1.2;
            Ionimg_WaitTillVolDone( iMSec);
            }
        }
    return rt;
    } extern BOOL Ionimg_WaitTillVolDone( int iTimeoutMs)
    {
    HARDWR_IMAGE_ENTRY   *FastZStatImg =
                         &(HardWrImgTable[
FAST_Z_NODE_ADDR].NVImg[FASTZ_OPSTATUS_NV_ADDR]);
    BOOL        rt = FALSE;
    int         iCt, iLoops, LoopTime, iLoopTick;

if( FastZStatImg->UpdatedFlg == TRUE)
        {
        switch( FastZStatImg->iNVValue)
```

```
            {
        case HDWR_VOL_STAT_UNDERFLOW:
                break;
        case HDWR_VOL_STAT_COMPL:
                rt = TRUE;
                break;
            }
        }
    if( FastZStatImg->UpdatedFlg == FALSE || FastZStatImg->iNVValue == HDWR_VOL_STAT_RDY)
        {
        FastZStatImg->UpdatedFlg = FALSE;
        LoopTime = VOL_CHK_LOOP_TIME;
        iLoopTick = LoopTime * CLK_TCK /1000;
        iLoops = iTimeoutMs / LoopTime;
        for( iCt = 0; iCt < iLoops && FastZStatImg->UpdatedFlg == FALSE; iCt++)
                {
                LonTimeBlockReadOneAndDecodeMsg( iLoopTick );
                if( FastZStatImg->UpdatedFlg == TRUE && FastZStatImg->iNVValue ==
HDWR_VOL_STAT_RDY)
                    FastZStatImg->UpdatedFlg = FALSE;
                }
        if( FastZStatImg->UpdatedFlg == TRUE &&
                                FastZStatImg->iNVValue == HDWR_VOL_STAT_COMPL)
                rt = TRUE;
        }
    return rt;
    }

/****************************************************
 * read surface data from SDP
 ****************************************************
 */
extern BOOL dat_ReadSurfaceFrSDP(void)
    {
    BOOL              rt = FALSE;
    IMAGE_DATA_SPEC   *ImgSpec = &(UVData.VolData.ImgSpec);
    int               CurrZ;

CurrZ = lonui_GetCommandedFastZPos();
    switch( UVData.Lon.eSDPAcq )
        {
        case eSDPAcqSurf:
        case eSDPAcqVol:
                if( UVData.Lon.eSDPAcq == eSDPAcqSurf)
                    {
                    rt = sdp_ReadSurfaceFrSDP( UVData.Lon.YDim, UVData.Lon.YDim,
                        (char *)UVData.VolData.SurfIByte,(char *)UVData.VolData.SurfZByte);
                    if( rt == TRUE)
                        {
                        if( UVData.VolData.VolByte)
                            UVData.VolData.VolByte = NULL;
                        sur_MowGrass( UVData.Lon.YDim, UVData.Lon.YDim,
UVData.VolData.SurfZByte,
```

```
                UVData.VolData.SurfTByte);
                        sur_SmoothSurface( UVData.Lon.YDim, UVData.Lon.YDim,
UVData.VolData.SurfZByte);
                                UpdateGlobalDataAfterSDP(ImgSpec, UVData.Lon.NumSlice);
                                UVData.NewVol    = eGlobalUpdate;
                                scr_UpdateFrGobalData( &UVData);
                                }
                        }
                        CurrZ = CurrZ - UVData.Lon.StartZStepOffset;
                        if( CurrZ < 0)
                          CurrZ = 0;
                        Ionui_SetFastZPos( CurrZ );
                        sdp_StopVol();
                        break;

case eSDPAcqSetRange:
                        rt = zr_ReadSurfAndSetRange( &UVData.Lon, CurrZ );
                        sdp_StopVol();
                    dat_SendInfoToWindows( eNewLonUIImg );
                        break;

default:        /* volume... this call is done after volume process */
                        CurrZ = CurrZ - UVData.Lon.StartZStepOffset;
                        if( CurrZ < 0)
                          CurrZ = 0;
                        Ionui_SetFastZPos( CurrZ );
                        sdp_StopVol();
                        break;

}
    UVData.Lon.eSDPAcq = eSDPAcqNone;

return rt;
    } static void warn_VolStopWarningCB( void * Parms, int NodeNum, int NVNum, int iValue)
    {
    int    CurrZ;
    switch( iValue)
      {
      case HDWR_VOL_STAT_COMPL:
                dat_ReadSurfaceFrSDP();
                break;
      case HDWR_VOL_STAT_UNDERFLOW:
                CurrZ = Ionui_GetCommandedFastZPos();
                Ionui_SetFastZPos( CurrZ);
                sdp_StopVol();
                break;
      }
    }
/****************************************************************
 * warning initialization
 ****************************************************************
```

```
*/
extern BOOL warn_Initialize( Widget TopBox)
{
WarnPack.bVisible = FALSE;
WarnPack.TopBox = TopBox;
WarnPack.Parms = NULL;                      /* dummy for now */
warn_RegisterWarning( eLonCBLaserInterlock, warn_InterlockWarningCB,&WarnPack);
warn_RegisterWarning( eLonCBCassetteSw,     warn_CassetteWarningCB, &WarnPack);
warn_RegisterWarning( eLonCBRobotInterlock, warn_RobotInterlockCB, &WarnPack);

warn_RegisterWarning( eLonCBVacStatus,      warn_VacWarningCB,     &WarnPack);
warn_RegisterWarning( eLonCBVolumeEnd,      warn_VolStopWarningCB, &WarnPack);

warn_RegisterWarning( eLonAPILaserResetStat, warn_LaserPwrResetCB,  &WarnPack);
warn_RegisterWarning( eLonAPIFastZResetStat, warn_FastZResetCB,     &WarnPack);
warn_RegisterWarning( eLonAPIPMTAmpResetStat,warn_PMTResetCB,       &WarnPack);
warn_RegisterWarning( eLonAPIPMTAmpClamped,  warn_PMTClampedCB,     &WarnPack);
return TRUE;
}
/**************************************************************
* Register API caller to warning callback structure
**************************************************************
*/
static BOOL warn_RegisterWarning( LON_API_WARNING_CB eWarn, WarnerFunc pCB, void
*WarnPac)
{
BOOL        rt= FALSE;

switch( eWarn)
   {
   case eLonCBLaserInterlock:
         rt =lonimg_RegisterCB( LASER_PWR_NODE_ADDR, LASER_INTERLOCK_NV_ADDR,
pCB, WarnPac);
         break;
   case eLonCBCassetteSw:
         rt =lonimg_RegisterCB( CASSETTE_SW_NODE_ADDR,
CASS_WAFER_PRES_NV_ADDR, pCB, WarnPac);
         if( rt == TRUE)
             rt =lonimg_RegisterCB( CASSETTE_SW_NODE_ADDR, CASS_SIZE_NV_ADDR,
                                                         pCB, WarnPac);

break;
   case eLonCBRobotInterlock:
         rt =lonimg_RegisterCB( CASSETTE_SW_NODE_ADDR, CASS_INTERLOCK_NV_ADDR,
pCB, WarnPac);
         break;
   case eLonCBVacStatus:
         /* rt =lonimg_RegisterCB ( SOLENOID_NODE_ADDR,
SOLENOID_DOOR_STAT_NV_ADDR, pCB, WarnPac);
         if( rt == TRUE)
         */
         rt =lonimg_RegisterCB( SOLENOID_NODE_ADDR,
SOLENOID_HOUSE_V_STAT_NV_ADDR, pCB, WarnPac);
         break;
   case eLonCBVolumeEnd:
```

-34-

```
                rt =Ionimg_RegisterCB( FAST_Z_NODE_ADDR, FASTZ_OPSTATUS_NV_ADDR, pCB,
WarnPac);
                break;
        case eLonAPILaserResetStat:
                rt =Ionimg_RegisterCB(LASER_PWR_NODE_ADDR,LASER_RESET_STAT_NV_ADDR,
pCB, WarnPac);
                break;
        case eLonAPIFastZResetStat:
                rt =Ionimg_RegisterCB( FAST_Z_NODE_ADDR, FASTZ_RESET_STAT_NV_ADDR, pCB,
WarnPac);
                break;
        case eLonAPIPMTAmpResetStat:
                rt =Ionimg_RegisterCB( PMT_AM_NODE_ADDR, PMTAM_RESET_STAT_NV_ADDR,
pCB, WarnPac);
                break;
        case eLonAPIPMTAmpClamped:
                rt =Ionimg_RegisterCB( PMT_AM_NODE_ADDR, PMTAM_CLAMPED_NV_ADDR, pCB,
WarnPac);
                break;
    }
    return rt;
 }
/**********************************************************************
 * register callback
 **********************************************************************
*/
extern BOOL Ionimg_RegisterCB( int NodeNum, int NetVar, void (*CBPtr)(), void *pParms)
{
  HARDWR_IMAGE_ENTRY  *NVImg;
  BOOL                rt = FALSE;
  CALLBK_STRUCT       *pCB, *pCBNew;

if( NodeNum < iNumNodeInSystem)
    {
    NVImg = &( HardWrImgTable[NodeNum].NVImg[ NetVar]);
    pCBNew = (CALLBK_STRUCT *)XtMalloc( sizeof( CALLBK_STRUCT));

pCBNew->CallBkPtr = CBPtr;
    pCBNew->ParmPtr   = pParms;
    pCBNew->NextCBPtr = NULL;
    if( NVImg->CBStructPtr == NULL)
         NVImg->CBStructPtr = pCBNew;
    else
       {
       for( pCB = NVImg->CBStructPtr; pCB->NextCBPtr != NULL; pCB = pCB->NextCBPtr)
              {};
       pCB->NextCBPtr = pCBNew;
       }
    rt = TRUE;
    }
  return rt;
 }
/**********************************************************************
 * read iZ mem from SDP
```

```
 * frame grabber always grab lines of 512,ie x dimension always 512
 * if caller wants less than 512, this function extracts
 * the center portions of the line
 ****************************************************************
 */
extern BOOL sdp_ReadSurfaceFrSDP( int iXDim, int iYDim, char *pI, char *pZ)
  {
  BOOL rt = FALSE;
  SDP_SURF_DATA    SurfParms;
  char   *TmpI = NULL, *TmpZ = NULL;
  int    iFrameSize, iSrcCt, iDestCt, iCt;

if( hSDP >= 0 && ( iXDim == 256 || iXDim == 512) )
      {
      iFrameSize = 512 * iYDim;
      TmpI = XtMalloc( iFrameSize);
      TmpZ = XtMalloc( iFrameSize);

SurfParms.iFrameSize = iFrameSize;
      SurfParms.IBuff      = TmpI;
      SurfParms.ZBuff      = TmpZ;
      if( ioctl( hSDP, eSDPCmdReadIZMem, &SurfParms) < 0)
            fprintf( stderr, "ioctl read surface data error.\n");
      else
            {
            if( iXDim == 512)
               {
               memcpy( pI, TmpI, iFrameSize);
               memcpy( pZ, TmpZ, iFrameSize);
               }
            else
               {
               iSrcCt = 0;                              /* left */
               for( iDestCt= 0, iCt= 0; iCt < iYDim; iCt++)
                     {
                     memcpy( &(pI[ iDestCt]), &(TmpI[ iSrcCt]), iXDim);
                     memcpy( &(pZ[ iDestCt]), &(TmpZ[ iSrcCt]), iXDim);
                     iDestCt += iXDim;
                     iSrcCt  += 512;
                     }
               }
            rt = TRUE;
            }
      XtFree( TmpI);
      XtFree( TmpZ);
      }
   return rt ;
   }
/***********************************************************
 * peak fit for a 7 point least sq and get max pos
 * least square curve fit to a quadratic form:
 * y = a(x*x) +bx + c
 * algorithm to solve for a,b,c in the least sq sense
 *
```

```
*  |y0|     |(x0*X0)  x0  1|
*  |y1|     |(x1*X1)  x1  1|
*  |y2|     |(x2*X2)  x2  1|  |a|
*  |y3|  =  |(x3*X3)  x3  1| *|b|
*  |y4|     |(x4*X4)  x4  1|  |c|
*  |y5|     |(x5*X5)  x5  1|
*  |y6|     |(x6*X6)  x6  1|
*
*  |y0|     |9 -3  1|
*  |y1|     |4 -2  1|
*  |y2|     |1 -1  1|  |a|
*  |y3|  =  |0  0  1| *|b|    for steps of 1 and arround center
*  |y4|     |1  1  1|  |c|    ie: x=-2,-1,-,1,2
*  |y5|     |4  2  1|
*  |y6|     |9  3  1|
*
*                    |y0|
*                    |y1|
*  | 9  4  1 0 1 4 9| |y2|      |196  0 28|  |a|
*  |-3 -2 -1 0 1 2 3|*|y3|  =  |  0 28  0| *|b|
*  | 1  1  1 1 1 1 1| |y4|      | 28  0  7|  |c|
*                    |y5|
*                    |y6|
*                                    |y0|
*                                    |y1|
*    1    | 1   0 -4|                |y2|   |a|
*  --- *  | 0   3  0|*| 9  4  1 0 1 4 9|*|y3| = |b|  inverted
*   84    |-4   0 28| |-3 -2 -1 0 1 2 3| |y4|   |c|
*                    | 1  1  1 1 1 1 1| |y5|
*                                    |y6|
*
*                                    |y0|
*                                    |y1|
*    1    | 5  0 -3 -4 -3  0  5|     |y2|   |a|
*  --- * |-9 -6 -3  0  3  6  9|*|y3| = |b|  inverted
*   84    |-8 12 24 28 24 12 -8|     |y4|   |c|
*                                    |y5|
*                                    |y6|
*
*  once a,b,c are found, then:
*                 2
*  Y = k(X- x0) + y0 = aX*X + bX + c
*                                          where x0 is the min/max position
*                                          max/min Y at X=x0
*  k = a
*  2kx0 = b
*  kx0x0 + y0 = c
*  therefore:
*       x0 = b/2k = b/2a
*       y0 = c - b*b/4a
*****************************************************************
*/
/****************************************************************
* peak fit for a 7 point least sq and get the max/min value
```

```
*****************************************************************
*/
extern BOOL util_PeakFit7PtsGetMaxValue( float *fData, int NumPoints, float *fPos)
{
  double a, b, c, fX0;
  BOOL rt = FALSE;

*fPos = fData[0];
  if( NumPoints == 7)
    {
    *fPos = ((double)fData[0] + fData[1] + fData[2] + fData[3] +
                     fData[4] + fData[5] + fData[6])   /7.0;
    a = (5.0 * fData[0]) - (3.0 * fData[2]) - (4.0* fData[3]) +
        (5.0 * fData[6])  - (3.0 * fData[4]);

b = (-9.0 * fData[0]) - ( 6.0 * fData[1]) - ( 3.0 * fData[2]) +
                    ( 9.0 * fData[6]) + ( 6.0 * fData[5]) +
                    (3.0* fData[4]);
    c = (-8.0 * fData[0]) +  (12.0 * fData[1]) + (24.0 * fData[2]) +
                    (28.0 * fData[3]) + (24.0 * fData[4]) +
                    (12.0 * fData[5]) - ( 8.0 * fData[6]);

if( a !=0)
        {
        fX0 = b / ( 2* a);              /* flat case */
        if( abs( fX0) < 3.1)
          *fPos = (c - ((b *b)/ ( 4.0 * a)))/84.0;
        rt = TRUE;
        }
    }
  return rt;
}
```

What is claimed is:

1. A method of obtaining an image of a surface with a confocal microscope having an objective lens, the surface comprised of a plurality of points, each of the points having a unique location represented by X, Y, and Z Cartesian coordinates, the method comprising the steps of:

selecting a first starting position for the objective lens along a Z vector from which to scan the surface, the Z vector substantially normal to the surface, the objective lens having a range of travel relative to the surface along the Z vector beginning at the first starting position;

dividing the range of travel into a plurality of Z positions along the Z vector, the plurality of Z positions including the starting position;

for each of the plurality of Z positions, positioning the objective lens at the Z position and scanning the surface to generate a plurality of signals, each of the signals corresponding to a given one of the points on the surface and representing an intensity of light reflected through the objective lens from the given point;

for each of the points on the surface, finding the Z coordinate of the point by determining which of the plurality of Z positions results in a maximum signal for the point, wherein the maximum signal, when correlated to the Z position of the objective lens, gives the Z location of the point on the surface;

comparing the Z locations of the points on the surface to determine a low point on the surface and a high point on the surface; and selecting a second starting position and a stopping position based on the high point and the low point.

2. The method of claim 1, wherein the microscope includes a photodetector having variable gain, the method further comprising the step of setting the photodetector gain between predetermined limits before scanning the surface.

3. The method of claim 1, wherein the step of selecting a first starting position includes the step of automatically focusing the microscope on the surface.

4. The method of claim 2, wherein each of the maximum signals represents a maximum intensity value of reflected light for a particular point on the surface, the method further comprising the step of smoothing the maximum intensity values by dividing the maximum intensity values into groups of maximum intensity values and averaging the maximum intensity values in each group to create a collection of group intensity values.

5. The method of claim 4, further comprising the steps of:

comparing the group intensity values to determine a maximum group intensity value; and resetting the photodetector gain based on the maximum group intensity value.

6. The method of claim 4, further comprising the steps of:

comparing each of the group intensity values to a threshold intensity value; and for each group intensity value below the threshold intensity value, setting each of the Z values corresponding to maximum intensity values in the group to an average Z value.

7. The method of claim 1, the step of selecting a second starting position and a second scan range further comprising the steps of:

calculating a safety margin using the high point and the low point;

adding the safety margin to the high point to determine the second starting point; and subtracting the safety margin from the low point to determine the stopping point.

8. The method of claim 7, wherein the safety margin is 2.5 microns plus twenty percent (20%) of the difference between the high point and the low point.

9. The method of claim 1, wherein the Z locations of the points on the surface are stored as an array of Z values.

10. The method of claim 9 further comprising the step of smoothing the Z values by dividing the array of Z values into groups of Z values and averaging the Z values in each of the groups to create a collection of group-averaged Z values.

* * * * *